(12) United States Patent
Flasinski et al.

(10) Patent No.: US 9,441,231 B2
(45) Date of Patent: Sep. 13, 2016

(54) CHIMERIC AND PROLINE RICH PROTEIN PROMOTERS FOR EXPRESSION IN PLANTS

(75) Inventors: Stanislaw Flasinski, Chesterfield, MO (US); Shirley Xiaoli Guo, Chesterfield, MO (US); Wei Wu, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1373 days.

(21) Appl. No.: 12/329,303

(22) Filed: Dec. 5, 2008

(65) Prior Publication Data
US 2009/0151020 A1 Jun. 11, 2009

Related U.S. Application Data

(60) Provisional application No. 60/992,605, filed on Dec. 5, 2007.

(51) Int. Cl.
*C12N 15/82* (2006.01)

(52) U.S. Cl.
CPC ....... *C12N 15/8216* (2013.01); *C12N 15/8227* (2013.01); *C12N 15/8279* (2013.01)

(58) Field of Classification Search
USPC .............. 435/6.1, 468, 419, 320.1; 530/370; 536/24.1; 800/278, 295
See application file for complete search history.

(56) References Cited

U.S. PATENT DOCUMENTS

| | | | | |
|---|---|---|---|---|
| 6,632,792 | B2* | 10/2003 | Schnepf et al. | 514/21.2 |
| 7,122,721 | B1* | 10/2006 | Duwenig et al. | 435/69.1 |
| 7,141,427 | B2* | 11/2006 | Mirkov et al. | 435/468 |
| 2002/0144306 | A1* | 10/2002 | Liang et al. | 800/279 |
| 2005/0003479 | A1* | 1/2005 | Wang et al. | 435/69.1 |
| 2005/0283856 | A1* | 12/2005 | Conner et al. | 800/300 |

FOREIGN PATENT DOCUMENTS

| | | | |
|---|---|---|---|
| WO | WO 91/13991 | * | 9/1991 |
| WO | WO 2004/085619 | | 10/2004 |
| WO | WO 2005/069986 | | 8/2005 |
| WO | WO 2005/069986 A2 | * | 8/2005 |

OTHER PUBLICATIONS

Tyler_Trends Genet_17_611_2001.*
Crane_Phil Trans Biol Sci_359_735_2004.*
Jakoby_Trends Plant Sci_7_106_2002.*
Zhang et al_abstract_2006.*
Potenza_In Vitro Cell Dev Biol Plant_40_1_2004.*
Cao_PNAS_95_6531_1988.*
Kay_Science_236_1299_1987.*
Rathus_Plant Mol Biol_23_613_1993.*
Steele et al., Am J Bot 97(7):1142-55 (2010).*
Showalter et al., Plant Physiol 153:485-513 (2010).*
JCVenter Inst_M. truncatula Genome Project_2015.*
Dvorakova et al., BMC Genom 8:412 (2007).*
Potenza et al., In Vitro Cell Dev Biol Plant 40:1-22 (2004).*
Deutch & Winicov, Plant Mol Biol 27:411-18 (1995).*
Keller, Plant Physiol 101:1227-30 (1993).*
AF028841.1 (1999).*
Elliott & Shirsat, Plant Mol Biol 37:675-87 (1998).*
Benfey et al., "The CaMV 35S enhancer contains at least two domains which can confer different developmental and tissue-specific expression patterns," *The EMBO J.*, 8(8):2195-2202, 1989.
Cho et al., "Regulation of root hair initiation and expansin gene expression in arabidopsis," *The Plant Cell*, 14:3237-3253, 2002.
Dai et al., "Improved plant-based production E1 endoglucanase using potato: expression optimization and tissue targeting," *Molecular Breeding*, 6:277-285, 2000.
Kay et al., "Duplication of CaMV 35S promoter sequences creates a strong enhancer for plant genes," *Science*, 236:1299-1302, 1987.
Kim et al., "A 20 nucleotide upstream element is essential for the nopaline synthase (nos) promoter activity," *Plant Molecular Biology*, 24:105-117, 1994.
Odell et al., "Identification of DNA sequences required for activity of the cauliflower mosaic virus 35S promoter," *Nature*, 313:810-812, 1985.
Piechulla et al., "Identification of tomato Lhc promoter regions necessary for circadian expression," *Plant Molecular Biology*, 38:655-662, 1998.
Welsch et al., "Structural and functional characterization of the phytoene synthase promoter from arabidopsis thaliana," *Planta*, 216:523-534, 2003.
Winicov et al., "The MSPRP2 promoter enables strong heterologous gene expression in a root-specific manner and is enhanced by overexpression of Alfin 1," *Planta*, 219:925-935, 2004.
Zhao et al., "Expression analysis of the plasma membrane H+—ATPase pma4 transcription promoter from Nicotiana plumbaginifolia activated by the CaMV 35S promoter enhancer," *Plant Sci.*, 149:157-165, 1999.

* cited by examiner

*Primary Examiner* — Medina A Ibrahim
*Assistant Examiner* — Russell Boggs
(74) *Attorney, Agent, or Firm* — Dentons US LLP; T. K. Ball, Esq.; Carine M. Doyle, Esq.

(57) ABSTRACT

The present invention provides regulatory polynucleotide molecules isolated from plant proline rich protein genes and linked to a viral enhancer molecule. The invention further discloses compositions, polynucleotide constructs, transformed host cells, transgenic plants and seeds containing the regulatory polynucleotide sequences, and methods for preparing and using the same.

8 Claims, 3 Drawing Sheets

SEQUENCE LISTING

```
<160> NUMBER OF SEQ ID NOS: 47

<210> SEQ ID NO 1
<211> LENGTH: 539
<212> TYPE: DNA
<213> ORGANISM: Cauliflower mosaic virus

<400> SEQUENCE: 1
ccggatccgg tccgatgtga gacttttcaa caaagggtaa tatccggaaa cctcctcgga     60
ttccattgcc cagctatctg tcactttatt gtgaagatag tggaaaagga aggtggctcc    120
tacaaatgcc atcattgcga taaaggaaag gccatcgttg aagatgcctc tgccgacagt    180
ggtcccaaag atggaccccc acccacgagg agcatcgtgg aaaaagaaga cgttccaacc    240
acgtcttcaa agcaagtgga ttgatgtgat ggtccgattg agacttttca acaaagggta    300
atatccggaa acctcctcgg attccattgc ccagctatct gtcactttat tgtgaagata    360
```

-continued

| | |
|---|---|
| gtggaaaagg aaggtggctc ctacaaatgc catcattgcg ataaaggaaa ggccatcgtt | 420 |
| gaagatgcct ctgccgacag tggtcccaaa gatggacccc cacccacgag gagcatcgtg | 480 |
| gaaaaagaag acgttccaac cacgtcttca aagcaagtgg attgatgtga tagatctcc | 539 |

<210> SEQ ID NO 2
<211> LENGTH: 423
<212> TYPE: DNA
<213> ORGANISM: Figwort mosaic virus

<400> SEQUENCE: 2

| | |
|---|---|
| ccggatccaa ttctcagtcc aaagcctcaa caaggtcagg gtacagagtc tccaaaccat | 60 |
| tagccaaaag ctacaggaga tcaatgaaga atcttcaatc aaagtaaact actgttccag | 120 |
| cacatgcatc atggtcagta agtttcagaa aaagacatcc accgaagact aaagttagt | 180 |
| gggcatcttt gaaagtaatc ttgtcaacat cgagcagctg gcttgtgggg accagacaaa | 240 |
| aaaggaatgg tgcagaattg ttaggcgcac ctaccaaaag catctttgcc tttattgcaa | 300 |
| agataaagca gattcctcta gtacaagtgg ggaacaaaat aacgtggaaa agagctgtcc | 360 |
| tgacagccca ctcactaatg cgtatgacga acgcagtgac gaccacaaaa gaattagatc | 420 |
| tcc | 423 |

<210> SEQ ID NO 3
<211> LENGTH: 2429
<212> TYPE: DNA
<213> ORGANISM: Medicago truncatula

<400> SEQUENCE: 3

| | |
|---|---|
| ataactcaca aggactaata ataagagaga acgaaagtgt acgtgagtgt aggagacacg | 60 |
| ttattataac attttatata tatttaaacg ttgataataa ttttgtcgat ctataaacca | 120 |
| ctaccaattc ctagttaaat atataataat tttattata tttgttagtt gatggtaaaa | 180 |
| gatgaatata atttgttact atatttttt ttgacaaaat aatttgttgc tatttaaaat | 240 |
| tcataaatat agtctataca tataatttta ataaaaataa aaattcaccc aaaaaaaaat | 300 |
| caaaaatttc ataaaaaaat aagtattgtt tataattcac gagcgttgtc gcagtacaaa | 360 |
| aatggataga tggataccca gtactagtaa ttaatgaagt taattggtaa aatttcactc | 420 |
| ttactggtgg ttgatggtag gggtgtttac ggtgcggttt ggttcggttt tgagagaaaa | 480 |
| agtcatccaa accgcaagat aaaaaaacat gcggtttgtg taacacccac agctgacgag | 540 |
| ggcaggggag tggtcaccgg tgcacaaggc acgccaatgg gcggctcccg acagcttcta | 600 |
| gaggaaccga atcacatctg aatgagaggg atcctgaggc cgtgtaggtg tgggactaca | 660 |
| tgaatgaagg aatgcttata agaattgttt ggtaatacct atatcaacaa ggtgcatctt | 720 |
| cttttttggta ccctattcca taagaactcc acagttaagc gtgcttgact tggagtagtc | 780 |
| tttggatggg tgacctaccg ggattcccga taagcatgcg agtgaggaca aacacgctga | 840 |
| aaagactcgt gttggtttgt agggtcagtc gacaatgctt aaagtcgtct gggatgttac | 900 |
| agtttggttt ggttcggttg gctttaaaat aaaatccgaa ccaaaccaaa ccaatatggt | 960 |
| ttgggttgta tcggttggtg cggttttttt cgtgacgata cgattttttg tttccaacat | 1020 |
| taagatcaag ataaaaagct gaaacacaat atattttcaa caatgttttta aatttcatca | 1080 |
| aacattacaa tttcatttttc attacaatgt ttccaacaac ataaaccaaa ttaaaaacgc | 1140 |
| ggacaaaaag taatcttatt ttgtaagaaa tgcaaaagac tgagatgttc tcattctcta | 1200 |

```
aaagttaagt agcacataaa tacatttta  aataaaagc aaataatgaa cttaacaaga    1260 gaaaaaaat  atgacattt  ataaaagttt tcattgagtt tctatgagta ttggtcttga    1320
tgacatatgt ttaattaaca ttttttctat gttacggttt ggtttggttt tgtatctatt    1380
tgacagtctc tttgtacttt gagcgacctc tttagtacgc cttatgctaa agaggtgtct    1440
ctcttattgt gaatatatat catttacct  tcttaaaaaa aagttaattg gtaaaaaaaa    1500 aaaaattct  ctcttgattt atatgaaata cattttttt  tggaacatgg agggtattga    1560
tttttacacc ttttcaaaag ccactcaagg atgaatatag attttcatg catcaaacac     1620 aagaatcatt agcataacat gctttggaaa acacacacat atacttaaat taatggttgg    1680
agtatcaaat ttaaaatat  tgttgtcaat acatacccg  tcaatcctcc ttttttaccc    1740
aataaacatt gaaatgttgc ttctttcgtt aagcataaaa acatcaaagt ctagcaaaat    1800 gttgttttttg cgatgacaca tttcatatag tttaaggat gcatgattcg attacaaaaa   1860
caaaatacta ataattctag cacaaagttt aaagctaaga ttataaagct tcatagcatg    1920
tggatattca tttagaaata taggattagg attgcccctt tcatcacggg tctaatagca    1980
ccacttgtca ctacatgtta aaaatgtcct ctagtacaac accgcttttt acttgattcc    2040
ccttgtccat gaaaaaatca aacaatattt ggacacaaaa atttgccccc actttccttt    2100
ttcttctgcc ctagtttgtt tgaaaactca tattgatcta atttggctat ggattcaaac    2160
aaaaaattca ctctgcccat tgcatgtgtg ggacccacat atgaatccgt gaaggatttc    2220
aatgtccatc caagtcaatg attcaacata taacattgaa taatttaatt ccaatttgca    2280
gtattatgat ttagattgat tgctgcaata cggtccgtga atgtaactca cgagaaagag    2340
gtatcaaggt atttattt  attttaaca aataaaattt cgaggtcttg ttcaccatat      2400
aaacctcctc actctcactc aattctctt                                     2429

<210> SEQ ID NO 4
<211> LENGTH: 593
<212> TYPE: DNA
<213> ORGANISM: Medicago truncatula

<400> SEQUENCE: 4
ggatgcatga ttcgattaca aaacaaaat actaataatt ctagcacaaa gtttaaagct      60
aagattataa agcttcatag catgtggata ttcatttaga aatataggat taggattgcc    120
cctttcatca cgggtctaat agcaccactt gtcactacat gttaaaaatg tcctctagta    180
caacaccgct ttttacttga ttccccttgt ccatgagaaa atcaaacaat atttggacac    240
aaaaatttgc cccactttc  cttttcttc  tgccctagtt tgtttgaaaa ctcatattga    300
tctagtttgg ctatggattc aaacaaaaaa ttcactctgc ccattgcatg tgtgggaccc    360
acatatgaat ccgtgaagga tttcaatgtc catccaagtc aatgattcaa catataacat    420 tgaataatt  aattccaatt tgcagtatta tgatttagat tgattgctgc aatacggtcc    480
gtgaatgtaa ctcacgagaa agaggtatca aggtatttta ttttatttt  aacaaataaa    540 atttcgaggt cttgttcacc atataaacct cctcactctc actcaattct ctt            593

<210> SEQ ID NO 5
<211> LENGTH: 2472
<212> TYPE: DNA
<213> ORGANISM: Medicago truncatula

<400> SEQUENCE: 5
ataactcaca aggactaata ataagagaga acgaaagtgt acgtgagtgt aggagacacg      60
```

```
ttattataac atttttataaa tatttaaacg ttgataataa ttttgtcgat ctataaacca      120
ctaccaattc ctagttaaat atataataat ttttattata tttgttagtt gatggtaaaa      180
gatgaatata atttgttact atattttttt ttgacaaaat aatttgttgc tatttaaaat      240
tcataaatat agtctataca tataatttta ataaaaataa aaattcaccc aaaaaaaaat      300 caaaatttc ataaaaaat aagtattgtt tataattcac gagcgttgtc gcagtacaaa       360
aatggataga tggataccca gtactagtaa ttaatgaagt taattggtaa aatttcactc     420
ttactggtgg ttgatggtag gggtgtttac ggtgcggttt ggttcggttt tgagagaaaa     480
agtcatccaa accgcaagat aaaaaaacat gcggtttgtg taacacccac agctgacgag     540
ggcaggggag tggtcaccgg tgcacaaggc acgccaatgg gcggctcccg acagcttcta     600
gaggaaccga atcacatctg aatgagaggg atcctgaggc cgtgtaggtg tgggactaca     660
tgaatgaagg aatgcttata agaattgttt ggtaatacct atatcaacaa ggtgcatctt     720 cttttttggta ccctattcca taagaactcc acagttaagc gtgcttgact tggagtagtc    780
tttggatggg tgacctaccg ggattcccga taagcatgcg agtgaggaca aaacacgctg     840
aaaagactcg tgttggtttg tagggtcagt cgacaatgct taaagtcgtc tgggatgtta     900
cagtttggtt tggttcggtt ggcttttaaaa taaaatccga accaaaccaa accaatatgg    960
tttgggttgt atcggttggt gcggtttttt cgtgacgata cgattttttg tttccaacat    1020
taaaatcaag ataaaaagct gaaacacaat atattttcaa caatgtttta aatttcatca    1080
aacattacaa tttcattttc attacaatgt ttccaacaac ataaaccaaa ttaaaaacgc    1140
ggacaaaaag taatcttatt ttgtaagaaa tgcaaaagac tgagatgttc tcattctcta    1200
aaagttaagt agcacataaa tacatttta aataaaaagc aaataatgaa cttaacaaga     1260
gaaaaaaaat atgacatttt ataaaagttt tcattgagtt tctatgagta ttggtcttga    1320
tgacatatgt ttaattaaca tttttcttat gttacggttt ggtttggttt tgtatctatt    1380
tgacagtctc tttgtacttt gagcgacctc tttagtacgc cttatgctaa agaggtgtct    1440
ctcttattgt gaatatatat cattttacct tcttaaaaaa aagttaattg gtaaaaaaaa    1500
aaaaatttct ctcttgattt atatgaaatg acattttttt tggaacatgg agggtattga    1560
tttttacacc ttttcaaaag ccactcaagg atgaatatag atttttcatg catcaaacac    1620
aagaatcatt agcataacat gctttggaaa acacacacat atacttaaat taatggttgg    1680
agtatcaaat ttaaaatat tgttgtcaat acatacccg tcaatcctcc ttttttaccc      1740
aataaacatt gaaatgttgc ttctttcgtt aagcataaaa acatcaaagt ctagcaaaat    1800 gttgttttt cgatgacaca tttcatatag tttaaaggat gcatgattcg attacaaaaa     1860
caaaatacta ataattctag cacaaagttt aaagctaaga ttataaagct tcatagcatg    1920
tggatattca tttagaaata taggattagg attgcccctt tcatcacggg tctaatagca    1980
ccacttgtca ctcatgtta aaatgtcct ctagtacaac accgctttt acttgattcc       2040 ccttgtccat gaaaaaatca aacaatattt ggacacaaaa atttgccccc actttccttt    2100
ttcttctgcc ctagtttgtt tgaaaactca tattgatcta atttggctat ggattcaaac    2160
aaaaaattca ctctgcccat tgcatgtgtg ggacccacat atgaatccgt gaaggatttc    2220
aatgtccatc caagtcaatg attcaacata taacattgaa taatttaatt ccaatttgca    2280
gtattatgat ttagattgat tgctgcaata cggtccgtga atgtaactca cgagaaagag    2340
gtatcaaggt attttatttt attttttaaca aataaaattt caaggtcttg ttcaccatat    2400
```

-continued

| aaacctcctc actctcactc aattctctta agtgtaagac ttcatagtaa actacactac | 2460 |
| tttcttaaa aa | 2472 |

<210> SEQ ID NO 6
<211> LENGTH: 636
<212> TYPE: DNA
<213> ORGANISM: Medicago truncatula

<400> SEQUENCE: 6

| ggatgcatga ttcgattaca aaaacaaaat actaataatt ctagcacaaa gtttaaagct | 60 |
| aagattataa agcttcatag catgtggata ttcatttaga aatataggat taggattgcc | 120 |
| cctttcatca cgggtctaat agcaccactt gtcactacat gttaaaaatg tcctctagta | 180 |
| caacaccgct ttttacttga ttccccttgt ccatgaaaaa atcaaacaat atttggacac | 240 |
| aaaaatttgc ccccactttc cttttttcttc tgccctagtt tgtttgaaaa ctcatattga | 300 |
| tctaatttgg ctatggattc aaacaaaaaa ttcactctgc ccattgcatg tgtgggaccc | 360 |
| acatatgaat ccgtgaagga tttcaatgtc catccaagtc aatgattcaa catataacat | 420 |
| tgaataattt aattccaatt tgcagtatta tgatttagat tgattgctgc aatacggtcc | 480 |
| gtgaatgtaa ctcacgagaa agaggtatca aggtatttta ttttattttt aacaaataaa | 540 |
| atttcgaggt cttgttcacc atataaacct cctcactctc actcaattct cttaagtgta | 600 |
| agacttcata gtaaactaca ctactttctt taaaaa | 636 |

<210> SEQ ID NO 7
<211> LENGTH: 2714
<212> TYPE: DNA
<213> ORGANISM: Medicago sativa

<400> SEQUENCE: 7

| gtcatctgga agatgagata ctactccctc cgtttcaaaa tgagtgtcgt tttaggtgtt | 60 |
| tacacgcata ttaagaaatg caatgattaa aagaaagaga atggttattt taccaaatta | 120 |
| tccttattaa ctattggtta gttttaaaag taatattttg gaagtagtgt gcagagtatt | 180 |
| aattgaaggg tacaattgaa aagaaaaagt tattattgca ttggaaactg aaagcgacat | 240 |
| tcattttgaa acaaattttt ttggctaaag cgacactcat tttgaaacgg agggagtacc | 300 |
| atttaagtga gttaatgtga tggaaaaaag ataaaatggt aatttaaca tacttcgtcc | 360 |
| catattaagt gacacaattg accttatcac acataccaat gcacaatttt gatgttaaat | 420 |
| aactttacta atctcttaga aaaaattata aaaatatgat attttaaaaa tactcattga | 480 |
| gacgaatcca acgacatctt atataatatt atttatctttt atatattagt agaaaaatgc | 540 |
| agtcaaaata tattaggtca atagtacacg ttttcaaatc atacacgttt ctgaaaaata | 600 |
| atggaagtag taattctttt aacgtttttg ttgttttaaa aaatacgtcc tccaatttta | 660 |
| taagcaatct ttgttttta aattcattaa ataattgatg tatctgaaat ataatataag | 720 |
| tcatatacgt cacttattta atgaatttga aaataacaaa aattgtatag atgtgaacag | 780 |
| aagaagtaca agataagtat cacccataga gtttttttt ttctctttat taacaaataa | 840 |
| aacaaacaca aatttagga gatatagata aaaaatatt tttcaaaagt aaacggactc | 900 |
| taatatttga taggaaccga tcgacaacaa aatagaatta tcaatcatgc tggaatttaa | 960 |
| tttgaagaag aaatgcaaac ctaaagagag gggggctaag taataccatg ctggaacttg | 1020 |
| aacaagaaaa accatgctct aagtaactaa gtaaggtagt acattacacc aattgagata | 1080 |
| agtacgacac attatgatga ttgagtgcta ttaaataaat gatgctgtag gagacacatt | 1140 |

```
attataactc acaaggacta ataataagag agaacgagag tgtacgtcag tgtaggagac    1200
acgttattat aacttttat aaatatttaa gctttgataa taattttgtc gatctatata     1260
taagccacta ccaatttaaa attatatata tatatatata tatatataa tatataataa    1320 tttttattat atttattacg ttgatggtaa aaaaataaat ataatttgtt accatttaaa    1380
agtcataaat atagtacaat ccaaccctt gagaggttaa tgtgtgtgcg gattttctag    1440
ataaacaagg tgccattcac gattcttctt ggtgcagctt ggagaaccct atcctgggct    1500
tggaagattt acttcttgtt gatgcttcta gagtacagct cttaaggctg tagtctagtt    1560
ttttttttca tccttctacc aaaaaaaaaa aagtcataaa tatagtttat acatataact    1620
ttaataaaaa taaaaaattt catccctaaa aacatagtag aaatttcata aaaaaaatat    1680
tgtttataat ttacatgcgt tagcagtaaa aaatggataa attgggtatg gagtactagt    1740
aattaataag gttcattggt taaaaaaact aaaaaataat ttctctcctg atttatatga    1800
aatgacattt ttttggaaca tgaagggtat tgatttttac accttttcaa aagccattca    1860
aggatgaata tagattttg gggcatcaaa cacaagaatc attagcataa catgctttgg    1920
aacacacaca tgcttaaatt aatggttgga gtatcaaatt ttaaaatatt gttgtcaata    1980 catacccgt caatcttctt ttttttaccc aataaacatt gaaatgttgc ttctttcgtt     2040
aagcataaaa acatcaaagt ctagcaaaat gttgttttg cgatgacaca tttcatatag    2100
tttaaaggat gcatgattcg attacaaaaa caaaatacta ataattctag cacaaagttt    2160
aaagcaagat tataaagctt catagcatgt ggatattcat ttagaaatat aggattagga    2220 ttgcccctt catcacgggt ctaacagcac cacttgtcac tacatgtcaa aaatgtcctc     2280
tagtacagca ccgctttta cttgattccc cttgtccatg catgaaaaaa atcaaaacaa    2340
tatttggaca cacaaacttg cccccacttt ccttttctt ctgccctagt ttgtttgaga     2400
ctcatattga tcaaatttgg ctatgaattc aaacaaaaaa ttcactctac ccattgcatg    2460 tgtgggccc acatataaat ccatgaagga tttcaatgtc catccaagtc aatgattcaa     2520
catatataac attgaataat ttaattccaa tttgcagtat tatgatttag attgattgct    2580
gcaatacggt ccgtgaatgt gatcactcac gagaagagg tatcaaaatt tcaaggtatt     2640
ttatttattt ttaacaaata aaatttcaag gtcttgttca ccatataaac ctcctcactc    2700
acacccaatt ctct                                                      2714
```

<210> SEQ ID NO 8
<211> LENGTH: 608
<212> TYPE: DNA
<213> ORGANISM: Medicago sativa

<400> SEQUENCE: 8

```
ggatgcatga ttcgattaca aaaacaaaat actaataatt ctagcacaaa gtttaaagca      60
agattataaa gcttcatagc atgtggatat tcatttagaa atataggatt aggattgccc     120
ctttcatcac gggtctaaca gcaccacttg tcactacatg tcaaaaatgt cctctagtac     180
agcaccgctt tttacttgat tcccttgtc catgcatgaa aaaatcaaa acaatatttg      240 gacacacaaa cttgcccca cttcctttt tcttctgccc tagttgtttt gagactcata       300
ttgatcaaat ttggctatga attcaaacaa aaaattcact ctacccattg catgtgtggg     360
gcccacatat aaatccatga aggatttcaa tgtccatcca agtcaatgat tcaacatata    420
taacattgaa taattaatt ccaatttgca gtattatgat ttagattgat tgctgcaata     480
```

```
cggtccgtga atgtgatcac tcacgagaaa gaggtatcaa aatttcaagg tattttattt      540
atttttaaca aataaaattt caaggtcttg ttcaccatat aaacctcctc actcacaccc      600
aattctct                                                               608
```

<210> SEQ ID NO 9
<211> LENGTH: 1229
<212> TYPE: DNA
<213> ORGANISM: Nicotiana plumbaginifolia

<400> SEQUENCE: 9

```
gcggccgccg cccggggatc ctcctggatg ccattttttcc tttgcttttg gatacctttt      60
cgcaacttta gtccattgct tgatatcgaa atagataatt tgaacccttta ccctatagtt     120 aatatcgaaa tagataatac aaaggagggg aacataaaac caaaacctcc gacaaaacat     180
caaagtgtag gagttcatga tatacgttga ttgaaagtgc acaatggtct ttgcatacta     240
tcaaagtacc aattggttct tgaattatat ctcttaatat aatgtattgt gtttaatttc     300
tctactattc cctattttat aagactaaaa gatcctgaca tgcttcttga acacatgtga     360
aggttagtta actggtcaga agtacacaag aattaatttg tacacctatg tttctgcacc     420
agaatgccat aaattacatc aattcttcaa catcaagtga tcgaaaaact taacaattgt     480
tctaatagtt gaactgagtc gtccgatcca tatccgattc ttcactagaa gcattaatca     540
tatagagcaa tttaacttaa tttactatat tggtaatcat ttacatagtt aagttataaa     600
accttggagc gacacaagga tttacactaa tcatgattga atattaactt tactcaattt     660
atcaatgtct gatacaagtg aattaatttc tctctttgtg atttcggtag aaaattaatg     720
tcaagtttca agttttttct ttttgaaatt agtcatacat gtgaatagaa cattaattta     780
agttaaagaa tcatataaaa aagttagccg ctttgatttc tgtaactgaa atcgtgcaga     840
gatgaggcat ccacacttgt ttttcaaagc ttcagtacta tttaaaaaca aagacagtaa     900
aaaggagact ttttctttga attattgcat cagaaatagt atagctgcca taatagttta     960
ttccttcgct tagcttgcag cctctatcaa acaaaaaaat acaccaactc aagtcaattt    1020
gagccgacaa catgacaaaa ccaaatcaaa tatgcctttt tttttttttt ttttttttt     1080 acactttggt aggtgttaag taatctagtg agactttac cttcatttat gaaaatcttg    1140
aaaagggtaa ttgtctaatt gaaagctata taagggggtc gaagtgaagc ttaagaggac    1200
aacaactttt ctcatttgtt tcaaagaac                                      1229
```

<210> SEQ ID NO 10
<211> LENGTH: 690
<212> TYPE: DNA
<213> ORGANISM: Oryza sativa

<400> SEQUENCE: 10

```
ccctatgtcc ctatctgtgg attgccagtg cgaatctcga cgtacgtggt ggcaaatgca      60
gccgcagtgc taggtggagc cccaagcggg cgtccaggtc gccggaaaac tccatggcgc     120
gctctggcgg tgtcaggtca cgggcgccat ggcgcgtccc atgcgacaa ccacctcagt     180 ctccccccct ccccgcagcg gcgtctcgac ctcatcgtct gtgcctgtgc gcgccgtgct     240
gccgagtgct agcgcgctag aagcgtcggc gcgcgtacgt ccgcgcgcgc gcgcggtgct     300
cgcccgtgag cgcccccgcg ccgtggccgc tagcgcgcgc gccccgggcc aggtggccgc     360
ctcgccggct cgccgcgaac acctggcgcc catccacgca tgcatccatg ccatgccatg     420
cacgagatga cgagacgaga ctgagttgat taattgatta acatacaagc tgcttggtta     480
```

```
gtgcagtgct ttgtgaactt gtgattggat caggtgttga ccatgggaga ttagtagcac    540
tagctagtgg cactgacagt agttcgtgtt cagtgtacgt gttcagtgtt cagtgatcag    600
cggaggcgtg ggcgtccatg gccgctctat aaaaggcgcg ccaacccatc tcacgccacc    660
gtgcaacgtc gagccgcgcc accagcatct                                      690

<210> SEQ ID NO 11
<211> LENGTH: 1256
<212> TYPE: DNA
<213> ORGANISM: Oryza sativa

<400> SEQUENCE: 11
tattcatgag ggattttca gggagggga gaggaacagc gagcgttgta cgttgggaga     60
agtgttgccc catgcgatgc cctcataacc cgttggagcc agcgacgatg agctgattcg    120
aggtggtggc ggtcgtcccg agttgctcca ctcgtggttg tcactgatcg aggcaagccc    180
aatgcctgat ctagcgagct cgacgaggca gcgacgatag cctagtgaga gcgtgcgcg    240 ggtgaggaga agggaagatg gaaatggtgg acgaagagga ggcggcggat ctagcgttta    300
ggacctcatt gttgtcccca ttccgtactg tcaagctcgt tgttgcccct cgaaccaacc    360
gatgttatcg tcgtgatcga cctatgaaga agcagctcga cgacgaccgc ctcgacctgt    420
ccgtagccgc tccgtcggag ctgccttgac ctcctcgtcg cttcttttcg tcgtcgtgtc    480
aatctcctcg atgttcaccc ggttcaaggc gatggcacta gggagctcgt tgttggagat    540
ggggagggga catcaacagc aattttagga aggaaaaag cgactatacc tcccactctc    600
tgccgctgag ctcatagtag tccaccttc ccacatcacc gagctcgtcg acgcgccgat    660
tagagtagga gagccaccga acagtcgtgg gccatgggag gacgagataa gagctgagat   720
gcggtcactg ccgtgggagg agtcgaggag agaatcgaga gagtgacgga agagggaaa    780 gagggggattt tattttttt ctagattctg gtattcattg ttaaattgtg tacttccaca    840
caaattgaaa taaatatgag agctagaata gatagtagca aggtctgaaa taaaaaaaac    900
aatgccattc ctagagccac ttacattata aaaagaataa ttttagactt atgaccctag    960
ctagacttcg tggtacagac gtacagtact ccaaggctca aatgaagatc ctgcactgtg   1020
agtgacggtc actcacgttg ccacacacac atgcataatt tccgagctac tagcactcta   1080
gcagctgcaa accctagagt tcacgggcca caacggcgag ctcgccactc tatataacca   1140
caccgccata aaccctagat cgatcgcaca aacacttcta gctcctcttc ttctccccc    1200 ccccccccc cccttctcac cacaacctgc tagcaagctc agagctagca gcagcc        1256

<210> SEQ ID NO 12
<211> LENGTH: 943
<212> TYPE: DNA
<213> ORGANISM: Pisum sativum

<400> SEQUENCE: 12
aagcttattt gatgaagttg ttgcatttta tttcctccat ttataatatt tgttaatttt    60
gtgtaaaatg acctattata gcaatttttt gtgaagctga gggaggattg gattttacac    120
ctattcaaaa gtcattcaaa gtttgtccct ccattcaagg atgaatgtag attttttcaag   180 catcaaacac aagaatcact agcataacat gctttgaaac ccacacactt aaattaatgt    240
taggaatatc aaatccaata taaaatcata gttgtcaatt acatactcaa tcaagtccct    300
ttcttttacc caataaacat caacatattg cttcttccat taagcatata aacatcaaag    360
```

| | |
|---|---|
| tctaaaacta gcaaaatgtt gttttagga tgacacattt catacatagt ttaaaagata | 420 |
| cttgattcga ttacaaaaag aaattaccaa tagtttagca caaagtctaa agcataatta | 480 |
| aagcatcaca tgtgcagatt tatgaaaaaa agattaagat tgccccttc atcacgggtc | 540 |
| gaataatagc actacttgtc actacatgtt aaaaaaatgt cctctagtac atcaaacttt | 600 |
| ttccattgat tcccttatc catgaaaaaa ataaacaaat tcttaagaca caaaaaaatg | 660 |
| gccccacatc cttttttctg cctagtttg tttgaattca ttctaactct tgaatatgta | 720 |
| acgaggccca ctaaaaatca atcaatgatt taacataaaa aatgaatagt ttaattccaa | 780 |
| tttgctgcaa catggtccgt gaatatgact cacgagaaag atatatcaaa atatcaaaat | 840 |
| ttcatagttt ttttcaccat ataaacctca tcactcattc tatttttta agtgcaaagc | 900 |
| ttcatagtag tgagcacaca cattacacta aaatcttcga aac | 943 |

<210> SEQ ID NO 13
<211> LENGTH: 925
<212> TYPE: DNA
<213> ORGANISM: Arabidopsis thaliana

<400> SEQUENCE: 13

| | |
|---|---|
| caaaatagag aatgggaggt gtatttaaag tcaataata atgacaaagt ctcttcttaa | 60 |
| attgtcgacc caattggcca ttacactaca aaaaccttg gttgctccca ttgttttcac | 120 |
| tctataatta caagtgtatg acttgtccaa cctttttttt aagttgtgtg ccaatactta | 180 |
| aacgatggct tttttttat gcgactaaac gtacgcttat agagtcggca ttctctaatt | 240 |
| aatgttagag tagagcttga aaatgtctct agctgattta tgcattgatt tctcgatata | 300 |
| tgtcagatat ttagcaattt gatctatgat atagctagaa aaataaggtg caagatataa | 360 |
| ttcttaaaag tagatagcat ttttcgaaat gctaactttt gaccaaatag gcaaatacga | 420 |
| acaatgaaat tttgtaaaga atatcacaat cgagctccct ttttatatat gatataaaaa | 480 |
| ggtttaagga atcgagatcg ttatatcgtt aaaaattgat aatctcttct ttcggagtat | 540 |
| ataagacaat aattaagcga atgtttatgc cgccgaatgc tgacaactat atcttacagt | 600 |
| ggtatttttg ttttttctaaa tattttatg ttccctcgta cgttaaatag tggctaaacc | 660 |
| cagtaatttt ttttgtaata tggatgagac aaatatatgc caattgagga aagtgtgaca | 720 |
| aaccctttgt tttcttttg taacaaagtg acctaatacg tgcttactca aatccaatt | 780 |
| caatcatcta aaccacaatt tggtgcatac aatatttata tataaaaatt aaatatctcg | 840 |
| tgagagtttt tctataaaag gtacacgtac actcatgtat ctacttactc actcctttca | 900 |
| gaaacccaaa ccctcattcc aaaaa | 925 |

<210> SEQ ID NO 14
<211> LENGTH: 1052
<212> TYPE: DNA
<213> ORGANISM: Arabidopsis thaliana

<400> SEQUENCE: 14

| | |
|---|---|
| tcaaaacttc acaaaacgta tgatacgatt aatgatagtt gtcagtgttt acttcagtac | 60 |
| ttgtaaaaaa gtcattgatc ctgaaatgga tggatctatg aatcagtttt gtgaagtcaa | 120 |
| tttttgttta caagtttaac tatttcgtcg ctgctaggat acatctgtaa ttaattcata | 180 |
| attaaacact aaccattatc attatttga cattaattat acataaatca tattgtagtt | 240 |
| tttttttttt ttttaaacat actatagcct tggacctagc tatatagaat tgattctctt | 300 |
| ttctctattt gtgcgtttgt tctggacaat atctaggcta caatatcaat aggtcgagac | 360 |

```
gaaagaacaa tagattccaa atttttttgcc taaaatccgc atgaacaagt gtacccaata      420
atcaaaggag cagaaaagag gaaggatctc tttatgtctt tgtggttttc tgaaaattga      480
gatgtctaat tcagtcaaat gataatgaca aattccttag ttagttgtct cgccacttgc      540
cattgttgtt tcagaaattg agaggtatct tttcagtcag ataataatga caaattcctt      600
cattatttgt cttgccatta gcaatacata aaaaaaaaat caatttgcat atagycccag      660
tctcataacc tttttgtttg tacgtggtaa atttacaaca ttttttaaact aagtacatac      720 gtaccattat tatcttgaac aattgaaatt tacaacaaaa aaattccgga agttttttac      780
tttttgtttt ctctttgata aaagaaaacc ttttttacttc ttatgaaaaa gtgacctgta      840
tattaatgta cttcatagta tagtccaact tcaataatct tactcgcaat ttggcacgtt      900
catatatcat cacggatgat gctaataagg acattattat acaaataaaa ataaatatct      960
tagagattac tgtggtctat aaaaagagga agacactcaa gtacttcatc acttccttgt     1020
cacaaaccaa accctaaacc atctttctca ac                                   1052

<210> SEQ ID NO 15
<211> LENGTH: 780
<212> TYPE: DNA
<213> ORGANISM: Zea mays

<400> SEQUENCE: 15
aactgatgat gagatgaaga ttcgagtcgt acgataagta ataaccagta aaaggctcat       60
acttaagcgg tgtttggttt ttagttatta attttaatc ctctaattta ttttattta      120 gtctataaat tatgaaaaat aaaatakagt tttagttttt tattagataa tttagagact     180
aaaatataat aaggagatgt ttggttttta gagactaatt tttagtcctt atattatatt     240
ctattttact ctttaaatta ccaaatacga aaactaaaac tctattatat atttagcaat     300
ttagggatta ataaaataa aataataaaa ctaaaaatta gtccatataa atcaaacacc      360
ctctaaaata aaatgaaagg actaaaaatt aagcttcttc tccgaccaag tggaccatgc     420
atgcttgcat tgtatcgttc attcttactg caaaagcgcc catatagcag catgcaacct     480
ggcatccatg tgctcgagca cgcaagcacg tactcgtagt acttgcatat ctactgatcg     540
aggtgtgcat gcacagcacg aaataaatgc agatcgccaa gaggatcaaa aattgaattc     600
agcttgatcc gatccgtcta gacggacagc gtggattcga gtaatttccc atctacaaaa     660
ccggcgcccg agcatctcct ttgtgaccaa tgaataactc atgcgcggtt cctgttcgtt     720
cgcgcctata aaagccatgg cgcagcaggg tcgatctcct ccactacaca caaacacaca     780

<210> SEQ ID NO 16
<211> LENGTH: 1125
<212> TYPE: DNA
<213> ORGANISM: Glycine max

<400> SEQUENCE: 16
cgaagaggta cgtgccaaat tacatcaatt tactacaact attactacta tttattatta       60
ttattattat tattattatt attattatta ttattattat tattattatt ataaacctgg      120
tgtctattat tttatgtact tgttcccatc atcaatatat attgtgtggg cggagttttc      180
taacaagatg tttgaaaata ataaatctta tcaagtatac tatgagtagt caagagaatc     240
aaaactagat catggaaatt accaaagcaa tttagcatga aagcctcggg tgttcgaggt     300
ttctaatcta acaaaatgtt cctgatttca atttagccaa ctgaattttt gagccaaata     360
```

```
ttgaatatgc agctggcagc catagtagcc aaactagttt gcaaatcgat ccgcatatgg    420
ggtagttaat taattagttt ctaatactgt tagtgttagg agcgttcctt cgttatgata    480
aaggaattca tgctttaatt tcccaatact tttgagcgag gtaggtttat ttcttgaaga    540
aaaaaaaatg tactaattaa gctaactcat gttatactta tattaccatt atatccatta    600
taaaaatctg accgcgtaga agaacaaatg atttgagttg gtaagaaaaa agtgatctga    660
gagctgacgt caaccaaata aattgtacaa aaaattacta gctctaattt ggtagatcta    720
aattctgcct cccacgctaa ttaagactat ggttatattc ttacacagca atcgttagtc    780
aaaacgattc aattatttaa tacggcaatt gaaattaatt atcctgaaat tccaacgcat    840
atagtacgtc ggtgcattga aaaaatggta agtaatatt  caaactggta cggaggtgtc    900
agtgttccct tttattttcc aacttccctt atccttacta aagaagaca  aagaaaaatc    960 accaactcaa ctacttgaca ttttttacaaa ggaacttaga tagctagcta ctgcgtcaaa   1020
ataattaact atagtatatt gagacttgca ccacttaaca gtgaggcccc gaactagtat   1080
aaaaacccat cattgggtgt gtgttattca ccagtaacta aaaac                   1125
```

<210> SEQ ID NO 17
<211> LENGTH: 1273
<212> TYPE: DNA
<213> ORGANISM: Glycine max

<400> SEQUENCE: 17

```
gtatacagta aatcgctact tgagtttaaa agtgtatata aatgtattgg taatattagt     60
ttaggtatta aatgaagtaa ttaaaacaaa gaatgatatg agttcagccc ataaatcatg    120
ttggttaacg tgtggaagtt aaaattgaat tatttagata ttatttaaat ttaattatta    180
gtagaaataa ttttaatta  aattttattt attttccgga caaactctgg attaatcaga    240
atagggtctc ttttttctga tgaatggaag ggttaaagaa aaaaaaaata actttcgttt    300
acgggcggtc atgcttgtga ttttggaatt gtttcaaaca aaatgggtgc gtggagtttt    360
ccaaaattgg ttgaaaagaa ttaaatttga tcaagtacta tgagtattca aggccaaatc    420
atggaaattg caaatgcaat tcaacaggaa agccttgttt gtgttaattt ctaatctaac    480
ataatgtttc taatttcaat ttagccaact caattttttga gccaaatatc atatatgttt    540
tcagttagag tagtttgcag atccgcatac gggccttaat tagtttatac tattatttag    600
tagcattcct tcattaggat taatggttta tttcttgaaa gaaagaaaaa aaaaaggtac    660
taaactatta actaataatt tacttatact accattatgt ccataaactt gatcagtaag    720
tgtataataa gtgatttgag cctagccaaa catagcaaat ctcatacaac taaagtatat    780
atgcagaaag catttcttgg ctctaatatg gtatatatct aaatcaattc tccagtgtta    840
agactctttt tctttgttag ttagcaatta atcatgagtc aaaaccagaa actagctact    900
acactcccat gccataatgc gtaaaacaat tcaattattt ggtatggcaa ttgaaattat    960
ttgtattaac acctttccaa aggagacaaa gacgtcggtg cattgagaaa ttgtgaaaaa   1020
aaaatattat cacttgtgtg gacttgtcaa tgttcccgtt aaatttccaa ctttgcaact   1080
acaagaagac agcattcacc tacacagcaa ttgaaaatcc acaccgaaga ttgacctttg   1140
tacaacggtg ctagaaaccg cgtcactagt aataactatt ggattgagac atgcacttaa   1200
cagtaaggcc cccaactaat ataaaaacca gttattgggt gtgttactca tcagcaacta   1260
caacgtgaga aac                                                      1273
```

<210> SEQ ID NO 18
<211> LENGTH: 671
<212> TYPE: DNA
<213> ORGANISM: Glycine max

<400> SEQUENCE: 18

```
gaattcgagc tcggtacccg ggatcgatcc tctagagtcg acctgcaggc atgcaagctt      60
gcggccgccc taggactagt ctcgaggcta gcccatgggg ccgggcccgg atcagtaagt     120
gtataataag tgatttgagc ctagccaaac atagcaaatc tcatacaact aaagtatata     180
tgcagaaagc atttcttggc tctaatatgg tatatatcta aatcaattct ccagtgttaa     240
gactcttttt ctttgttagt tagcaattaa tcatgagtca aaaccagaaa ctagctacta     300
cactcccatg ccataatgcg taaaacaatt caattatttg gtatggcaat tgaaattatt     360
tgtattaaca cctttccaaa ggagacaaag acgtcggtgc attgagaaat gtgaaaaaaa     420
aatattatca cttgtgtgga cttgtcaatg ttcccgttaa atttccaact ttgcaactac     480
aagaagacag cattcaccta cacagcaatt gaaaatccac accgaagatt gacctttgta     540
caacggtgct agaaaccgcg tcactagtaa taactattgg attgagacat gcacttaaca     600
gtaaggcccc caactaatat aaaaaccagt tattgggtgt gttactcatc agcaactaca     660
acgtgagaaa c                                                          671
```

<210> SEQ ID NO 19
<211> LENGTH: 1049
<212> TYPE: DNA
<213> ORGANISM: Artificial
<220> FEATURE:
<223> OTHER INFORMATION: Chimeric FMV35S-MtPrp sequence

<400> SEQUENCE: 19

```
aattctcagt ccaaagcctc aacaaggtca gggtacagag tctccaaacc attagccaaa      60
agctacagga gatcaatgaa gaatcttcaa tcaaagtaaa ctactgttcc agcacatgca     120
tcatggtcag taagtttcag aaaaagacat ccaccgaaga cttaaagtta gtgggcatct     180
ttgaaagtaa tcttgtcaac atcgagcagc tggcttgtgg ggaccagaca aaaaaggaat     240
ggtgcagaat tgttaggcgc acctaccaaa agcatctttg cctttattgc aaagataaag     300
cagattcctc tagtacaagt ggggaacaaa ataacgtgga aaagagctgt cctgacagcc     360
cactcactaa tgcgtatgac gaacgcagtg acgaccacaa agaattaga tccggatgca     420
tgattcgatt acaaaaacaa aatactaata attctagcac aaagtttaaa gctaagatta     480
taaagcttca tagcatgtgg atattcattt agaaatatag gattaggatt gcccctttca     540
tcacgggtct aatagcacca cttgtcacta catgttaaaa atgtcctcta gtacaacacc     600
gcttttact tgattcccct tgtccatgag aaaatcaaac aatatttgga cacaaaaatt     660
tgcccccact ttccttttc ttctgccctta gtttgtttga aaactcatat tgatctagtt     720
tggctatgga ttcaaacaaa aaattcactc tgcccattgc atgtgtggga cccacatatg     780
aatccgtgaa ggatttcaat gtccatccaa gtcaatgatt caacatataa cattgaataa     840
tttaattcca atttgcagta ttatgattta gattgattgc tgcaatacgg tccgtgaatg     900
taactcacga gaaagaggta tcaaggtatt ttattttatt tttaacaaat aaaatttcga     960
ggtcttgttc accatataaa cctcctcact ctcactcaat tctcttaagt gtaagacttc    1020
atagtaaact acactacttt ctttaaaaa                                      1049
```

<210> SEQ ID NO 20

<211> LENGTH: 1165
<212> TYPE: DNA
<213> ORGANISM: Artificial
<220> FEATURE:
<223> OTHER INFORMATION: Chimeric CaMV35S-MtPrp sequence

<400> SEQUENCE: 20

| | | | | | |
|---|---|---|---|---|---|
| ggtccgatgt | gagactttc | aacaaagggt | aatatccgga | aacctcctcg | gattccattg | 60 |
| cccagctatc | tgtcactta | ttgtgaagat | agtggaaaag | gaaggtggct | cctacaaatg | 120 |
| ccatcattgc | gataaaggaa | aggccatcgt | tgaagatgcc | tctgccgaca | gtggtcccaa | 180 |
| agatggaccc | ccacccacga | ggagcatcgt | ggaaaaagaa | gacgttccaa | ccacgtcttc | 240 |
| aaagcaagtg | gattgatgtg | atggtccgat | tgagactttt | caacaaaggg | taatatccgg | 300 |
| aaacctcctc | ggattccatt | gcccagctat | ctgtcacttt | attgtgaaga | tagtggaaaa | 360 |
| ggaaggtggc | tcctacaaat | gccatcattg | cgataaagga | aaggccatcg | ttgaagatgc | 420 |
| ctctgccgac | agtggtccca | aagatggacc | cccacccacg | aggagcatcg | tggaaaaaga | 480 |
| agacgttcca | accacgtctt | caaagcaagt | ggattgatgt | gatagatccg | gatgcatgat | 540 |
| tcgattacaa | aaacaaaata | ctaataattc | tagcacaaag | tttaaagcta | agattataaa | 600 |
| gcttcatagc | atgtggatat | tcatttagaa | atataggatt | aggattgccc | ctttcatcac | 660 |
| gggtctaata | gcaccacttg | tcactacatg | ttaaaaatgt | cctctagtac | aacaccgctt | 720 |
| tttacttgat | tcccccttgtc | catgagaaaa | tcaaacaata | tttggacaca | aaaatttgcc | 780 |
| cccactttcc | tttttcttct | gccctagttt | gtttgaaaac | tcatattgat | ctagtttggc | 840 |
| tatgattca | aacaaaaaat | tcactctgcc | cattgcatgt | gtgggaccca | catatgaatc | 900 |
| cgtgaaggat | ttcaatgtcc | atccaagtca | atgattcaac | atataacatt | gaataattta | 960 |
| attccaattt | gcagtattat | gatttagatt | gattgctgca | atacggtccg | tgaatgtaac | 1020 |
| tcacgagaaa | gaggtatcaa | ggtattttat | tttatttta | acaaataaaa | tttcgaggtc | 1080 |
| ttgttcacca | tataaacctc | ctcactctca | ctcaattctc | ttaagtgtaa | gacttcatag | 1140 |
| taaactacac | tactttcttt | aaaaa | | | | 1165 |

<210> SEQ ID NO 21
<211> LENGTH: 1219
<212> TYPE: DNA
<213> ORGANISM: Artificial Sequence
<220> FEATURE:
<223> OTHER INFORMATION: Chimeric CaMV35S-OsPrp sequence

<400> SEQUENCE: 21

| | | | | | |
|---|---|---|---|---|---|
| ggtccgatgt | gagactttc | aacaaagggt | aatatccgga | aacctcctcg | gattccattg | 60 |
| cccagctatc | tgtcactta | ttgtgaagat | agtggaaaag | gaaggtggct | cctacaaatg | 120 |
| ccatcattgc | gataaaggaa | aggccatcgt | tgaagatgcc | tctgccgaca | gtggtcccaa | 180 |
| agatggaccc | ccacccacga | ggagcatcgt | ggaaaaagaa | gacgttccaa | ccacgtcttc | 240 |
| aaagcaagtg | gattgatgtg | atggtccgat | tgagactttt | caacaaaggg | taatatccgg | 300 |
| aaacctcctc | ggattccatt | gcccagctat | ctgtcacttt | attgtgaaga | tagtggaaaa | 360 |
| ggaaggtggc | tcctacaaat | gccatcattg | cgataaagga | aaggccatcg | ttgaagatgc | 420 |
| ctctgccgac | agtggtccca | aagatggacc | cccacccacg | aggagcatcg | tggaaaaaga | 480 |
| agacgttcca | accacgtctt | caaagcaagt | ggattgatgt | gatgtcgacc | cctatgtccc | 540 |
| tatctgtgga | ttgccagtgc | gaatctcgac | gtacgtggtg | gcaaatgcag | ccgcagtgct | 600 |
| aggtggagcc | ccaagcgggc | gtccaggtcg | ccggaaaact | ccatggcgcg | ctctggcggt | 660 |

-continued

```
gtcaggtcac gggcgccatg gcgcgtccca tggcgacaac cacctcagtc tcccccctc    720 cccgcagcgg cgtctcgacc tcatcgtctg tgcctgtgcg cgccgtgctg ccgagtgcta   780
gcgcgctaga agcgtcggcg cgcgtacgtc cgcgcgcgcg cgcggtgctc gcccgtgagc   840
gccccccgcg cgtggccgct agcgcgcgcg ccccgggcca ggtggccgcc tcgccggctc   900
gccgcgaaca cctggcgccc atccacgcat gcatccatgc catgccatgc acgagatgac   960
gagacgagac tgagttgatt aattgattaa catacaagct gcttggttag tgcagtgctt  1020
tgtgaacttg tgattggatc aggtgttgac catgggagat tagtagcact agctagtggc  1080
actgacagta gttcgtgttc agtgtacgtg ttcagtgttc agtgatcagc ggaggcgtgg  1140
gcgtccatgg ccgctctata aaaggcgcgc caacccatct cacgccaccg tgcaacgtcg  1200
agccgcgcca ccagcatct                                               1219
```

<210> SEQ ID NO 22
<211> LENGTH: 1786
<212> TYPE: DNA
<213> ORGANISM: Artificial Sequence
<220> FEATURE:
<223> OTHER INFORMATION: Chimeric CaMV35S-OsPrp sequence

<400> SEQUENCE: 22

```
ggtccgatgt gagacttttc aacaaagggt aatatccgga aacctcctcg gattccattg    60
cccagctatc tgtcacttta ttgtgaagat agtggaaaag gaaggtggct cctacaaatg   120
ccatcattgc gataaaggaa aggccatcgt tgaagatgcc tctgccgaca gtggtcccaa   180
agatggaccc ccacccacga ggagcatcgt ggaaaaagaa gacgttccaa ccacgtcttc   240
aaagcaagtg gattgatgtg atggtccgat tgagactttt caacaaaggg taatatccgg   300
aaacctcctc ggattccatt gcccagctat ctgtcacttt attgtgaaga tagtggaaaa   360
ggaaggtggc tcctacaaat gccatcattg cgataaagga aaggccatcg ttgaagatgc   420
ctctgccgac agtggtccca agatggaccc ccacccacg aggagcatcg tggaaaaaga   480
agacgttcca accacgtctt caaagcaagt ggattgatgt gatgtcgaga tattcatgag   540
ggatttttca gggaggggga aggaacagc gagcgttgta cgttgggaga agtgttgccc   600
catgcgatgc cctcataacc cgttggagcc agcgacgatg agctgattcg aggtggtggc   660
ggtcgtcccg agttgctcca ctcgtggttg tcactgatcg aggcaagccc aatgcctgat   720
ctagcgagct cgacgaggca gcgacgatag cctagtgaga gacgtgcgcg ggtgaggaga   780
agggaagatg gaaatggtgg acgaagagga ggcggcggat ctagcgttta ggacctcatt   840
gttgtcccca ttccgtactg tcaagctcgt tgttgccct cgaaccaacc gatgttatcg   900
tcgtgatcga cctatgaaga agcagctcga cgacgaccgc ctcgacctgt ccgtagccgc   960
tccgtcggag ctgccttgac ctcctcgtcg cttcttttcg tcgtcgtgtc aatctcctcg  1020
atgttcaccc ggttcaaggc gatggcacta gggagctcgt tgttggagat gggggaggga  1080
catcaacagc aattttagga aaggaaaaag cgactatacc tcccactctc tgccgctgag  1140
ctcatagtag tccacccttc ccacatcacc gagctcgtcg acgcgccgat tagagtagga  1200
gagccaccga acagtcgtgg gccatgggag gacgagataa gagctgagat gcggtcactg  1260
ccgtgggagg agtcgaggag agaatcgaga gagtgacgga gagggggaaa gagggggattt  1320 tatttttttt ctagattctg gtattcattg ttaaattgtg tacttccaca caaattgaaa  1380
taaatatgag agctagaata gatagtagca aggtctgaaa taaaaaaac aatgccattc   1440
```

-continued

| | |
|---|---|
| ctagagccac ttacattata aaaagaataa ttttagactt atgaccctag ctagacttcg | 1500 |
| tggtacagac gtacagtact ccaaggctca aatgaagatc ctgcactgtg agtgacggtc | 1560 |
| actcacgttg ccacacacac atgcataatt tccgagctac tagcactcta gcagctgcaa | 1620 |
| accctagagt tcacgggcca caacggcgag ctcgccactc tatataacca caccgccata | 1680 |
| aaccctagat cgatcgcaca aacacttcta gctcctcttc ttctcccccc cccccccccc | 1740 |
| cccttctcac cacaacctgc tagcaagctc agagctagca gcagcc | 1786 |

<210> SEQ ID NO 23
<211> LENGTH: 1472
<212> TYPE: DNA
<213> ORGANISM: Artificial Sequence
<220> FEATURE:
<223> OTHER INFORMATION: Chimeric CaMV35S-PsPrp sequence

<400> SEQUENCE: 23

| | |
|---|---|
| ggtccgatgt gagactttc aacaaagggt aatatccgga aacctcctcg gattccattg | 60 |
| cccagctatc tgtcactta ttgtgaagat agtggaaaag gaaggtggct cctacaaatg | 120 |
| ccatcattgc gataaaggaa aggccatcgt tgaagatgcc tctgccgaca gtggtcccaa | 180 |
| agatggaccc ccaccacga ggagcatcgt ggaaaagaa gacgttccaa ccacgtcttc | 240 |
| aaagcaagtg gattgatgtg atggtccgat tgagactttt caacaaaggg taatatccgg | 300 |
| aaacctcctc ggattccatt gcccagctat ctgtcacttt attgtgaaga tagtggaaaa | 360 |
| ggaaggtggc tcctacaaat gccatcattg cgataaagga aaggccatcg ttgaagatgc | 420 |
| ctctgccgac agtggtccca agatggaccc ccaccacg aggagcatcg tggaaaaga | 480 |
| agacgttcca accacgtctt caaagcaagt ggattgatgt gatgtcgaca gcttatttg | 540 |
| atgaagttgt tgcattttat ttcctccatt tataatattt tgttaatttg tgtaaaatga | 600 |
| cctattatag caatttttg tgaagctgag ggaggattgg atttacacc tattcaaaag | 660 |
| tcattcaaag tttgtccctc cattcaagga tgaatgtaga ttttttcaagc atcaaacaca | 720 |
| agaatcacta gcataacatg ctttgaaacc cacacactta aattaatgtt aggaatatca | 780 |
| aatccaatat aaaatcatag ttgtcaatta catactcaat caagtcccttt tcttttaccc | 840 |
| aataaacatc aacatattgc ttcttccatt aagcatataa acatcaaagt ctaaaactag | 900 |
| caaaatgttg ttttttaggat gacacatttc atacatagtt taaagatac ttgattcgat | 960 |
| tacaaaaaga aattaccaat agtttagcac aaagtctaaa gcataattaa agcatcacat | 1020 |
| gtgcagattt atgaaaaaaa gattaagatt gccccttttca tcacgggtcg aataatagca | 1080 |
| ctacttgtca ctacatgtta aaaaaatgtc ctctagtaca tcaaactttt tccattgatt | 1140 |
| ccccttatcc atgaaaaaaa taaacaaatt cttaagacac aaaaaaatgg ccccacatcc | 1200 |
| tttttttctgg cctagtttgt ttgaattcat tctaactctt gaatatgtaa cgaggcccac | 1260 |
| taaaaatcaa tcaatgattt aacataaaaaa atgaatagtt taattccaat ttgctgcaac | 1320 |
| atggtccgtg aatatgactc acgagaaaga tatatcaaaa tatcaaaatt tcatagtttt | 1380 |
| tttcaccata taaacctcat cactcattct atttttttaa gtgcaaagct tcatagtagt | 1440 |
| gagcacacac attacactaa aatcttcgaa ac | 1472 |

<210> SEQ ID NO 24
<211> LENGTH: 1654
<212> TYPE: DNA
<213> ORGANISM: Artificial Sequence
<220> FEATURE:
<223> OTHER INFORMATION: Chimeric CaMV35S-GmPrp sequence

<400> SEQUENCE: 24

```
ggtccgatgt gagactttc aacaaagggt aatatccgga aacctcctcg gattccattg      60
cccagctatc tgtcactta ttgtgaagat agtggaaaag gaaggtggct cctacaaatg     120
ccatcattgc gataaaggaa aggccatcgt tgaagatgcc tctgccgaca gtggtcccaa    180
agatggaccc ccacccacga ggagcatcgt ggaaaaagaa gacgttccaa ccacgtcttc    240
aaagcaagtg gattgatgtg atggtccgat tgagactttt caacaaaggg taatatccgg    300
aaacctcctc ggattccatt gcccagctat ctgtcacttt attgtgaaga tagtggaaaa    360
ggaaggtggc tcctacaaat gccatcattg cgataaagga aaggccatcg ttgaagatgc    420
ctctgccgac agtggtccca agatggaccc ccacccacg aggagcatcg tggaaaaaga    480
agacgttcca accacgtctt caaagcaagt ggattgatgt gatgtcgacc gaagaggtac    540
gtgccaaatt acatcaattt actacaacta ttactactat ttattattat tattattatt    600
attattatta ttattattat tattattatt attattatta taaacctggt gtctattatt    660
ttatgtactt gttcccatca tcaatatata ttgtgtgggc ggagtttct aacaagatgt     720
ttgaaaataa taaatcttat caagtatact atgagtagtc aagagaatca aaactagatc    780
atggaaatta ccaaagcaat ttagcatgaa agcctcgggt gttcgaggtt tctaatctaa    840
caaaatgttc ctgatttcaa tttagccaac tgaattttg agccaaatat tgaatatgca     900
gctggcagcc atagtagcca actagtttg caaatcgatc cgcatatggg gtagttaatt     960
aattagtttc taatactgtt agtgttagga gcgttccttc gttatgataa aggaattcat   1020
gctttaattt cccaatactt tgagcgagg taggtttatt tcttgaagaa aaaaaatgt     1080
actaattaag ctaactcatg ttatacttat attaccatta tatccattat aaaaatctga   1140
ccgcgtagaa gaacaaatga tttgagttgg taagaaaaaa gtgatctgag agctgacgtc   1200
aaccaaataa attgtacaaa aaattactag ctctaatttg gtagatctaa attctgcctc   1260
ccacgctaat taagactatg gttatattct tacacagcaa tcgttagtca aaacgattca   1320
attatttaat acggcaattg aaattaatta tcctgaaatt ccaacgcata tagtacgtcg   1380
gtgcattgaa aaaatggtaa agtaatattc aaactggtac ggaggtgtca gtgttccctt   1440
ttatttccca acttcccta tccttactat aagaagacaa agaaaaatca ccaactcaac    1500
tacttgacat tttacaaag gaacttagat agctagctac tgcgtcaaaa taattaacta    1560
tagtatattg agacttgcac cacttaacag tgaggccccg aactagtata aaaacccatc   1620
attgggtgtg tgttattcac cagtaactaa aaac                                1654
```

<210> SEQ ID NO 25
<211> LENGTH: 1802
<212> TYPE: DNA
<213> ORGANISM: Artificial Sequence
<220> FEATURE:
<223> OTHER INFORMATION: Chimeric CaMV35S-GmPrp sequence

<400> SEQUENCE: 25

```
ggtccgatgt gagactttc aacaaagggt aatatccgga aacctcctcg gattccattg      60
cccagctatc tgtcactta ttgtgaagat agtggaaaag gaaggtggct cctacaaatg     120
ccatcattgc gataaaggaa aggccatcgt tgaagatgcc tctgccgaca gtggtcccaa    180
agatggaccc ccacccacga ggagcatcgt ggaaaaagaa gacgttccaa ccacgtcttc    240
aaagcaagtg gattgatgtg atggtccgat tgagactttt caacaaaggg taatatccgg    300
```

```
aaacctcctc ggattccatt gcccagctat ctgtcacttt attgtgaaga tagtggaaaa    360
ggaaggtggc tcctacaaat gccatcattg cgataaagga aaggccatcg ttgaagatgc    420
ctctgccgac agtggtccca agatggaccc ccacccacg aggagcatcg tggaaaaaga    480
agacgttcca accacgtctt caaagcaagt ggattgatgt gatgtcgacg tatacagtaa    540
atcgctactt gagtttaaaa gtgtatataa atgtattggt aatattagtt taggtattaa    600
atgaagtaat taaacaaag aatgatatga gttcagccca taaatcatgt tggttaacgt    660
gtggaagtta aaattgaatt atttagatat tatttaaatt taattattag tagaaataat    720
ttttaattaa atttttattta ttttccggac aaactctgga ttaatcagaa tagggtctct    780
tttttctgat gaatggaagg gttaaagaaa aaaaaaataa ctttcgttta cgggcggtca    840
tgcttgtgat tttggaattg tttcaaacaa aatgggtgcg tggagttttc caaaattggt    900
tgaaaagaat taaatttgat caagtactat gagtattcaa ggccaaatca tggaaattgc    960
aaatgcaatt caacaggaaa gccttgtttg tgttaatttc taatctaaca taatgttcct   1020
aatttcaatt tagccaactc aattttgag ccaaatatca tatatgtttt cagttagagt   1080
agtttgcaga tccgcatacg ggccttaatt agtttatact attatttagt agcattcctt   1140
cattaggatt aatggtttat ttcttgaaag aaagaaaaaa aaaggtact aaactattaa   1200 ctaataattt acttatacta ccattatgtc cataaacttg atcagtaagt gtataataag   1260
tgatttgagc ctagccaaac atagcaaatc tcatacaact aaagtatata tgcagaaagc   1320
atttcttggc tctaatatgg tatatatcta aatcaattct ccagtgttaa gactcttttt   1380
ctttgttagt tagcaattaa tcatgagtca aaaccagaaa ctagctacta cactcccatg   1440
ccataatgcg taaaacaatt caattatttg gtatggcaat tgaaattatt tgtattaaca   1500
cctttccaaa ggagacaaag acgtcggtgc attgagaaat tgtgaaaaaa aatattatc   1560 acttgtgtgg acttgtcaat gttcccgtta aatttccaac tttgcaacta caagaagaca   1620
gcattcacct acacagcaat tgaaaatcca caccgaagat tgacctttgt acaacggtgc   1680
tagaaaccgc gtcactagta ataactattg gattgagaca tgcacttaac agtaaggccc   1740
ccaactaata taaaaaccag ttattgggtg tgttactcat cagcaactac aacgtgagaa   1800
ac                                                                  1802

<210> SEQ ID NO 26
<211> LENGTH: 1200
<212> TYPE: DNA
<213> ORGANISM: Artificial Sequence
<220> FEATURE:
<223> OTHER INFORMATION: Chimeric CaMV35S-GmPrp  sequence

<400> SEQUENCE: 26
ggtccgatgt gagacttttc aacaaagggt aatatccgga aacctcctcg gattccattg     60
cccagctatc tgtcacttta ttgtgaagat agtggaaaag gaaggtggct cctacaaatg    120
ccatcattgc gataaaggaa aggccatcgt tgaagatgcc tctgccgaca gtggtcccaa    180
agatggaccc ccacccacga ggagcatcgt ggaaaaagaa gacgttccaa ccacgtcttc    240
aaagcaagtg gattgatgtg atggtccgat tgagactttt caacaaaggg taatatccgg    300
aaacctcctc ggattccatt gcccagctat ctgtcacttt attgtgaaga tagtggaaaa    360
ggaaggtggc tcctacaaat gccatcattg cgataaagga aaggccatcg ttgaagatgc    420
ctctgccgac agtggtccca agatggaccc ccacccacg aggagcatcg tggaaaaaga    480
agacgttcca accacgtctt caaagcaagt ggattgatgt gatgtcgacg aattcgagct    540
```

```
cggtacccgg gatcgatcct ctagagtcga cctgcaggca tgcaagcttg cggccgccct      600
aggactagtc tcgaggctag cccatggggc cgggcccgga tcagtaagtg tataataagt      660
gatttgagcc tagccaaaca tagcaaatct catacaacta agtatatat gcagaaagca       720 tttcttggct ctaatatggt atatatctaa atcaattctc cagtgttaag actcttttc       780 tttgttagtt agcaattaat catgagtcaa aaccagaaac tagctactac actcccatgc      840
cataatgcgt aaaacaattc aattatttgg tatggcaatt gaaattattt gtattaacac      900
ctttccaaag gagacaaaga cgtcggtgca ttgagaaatg tgaaaaaaaa atattatcac      960
ttgtgtggac ttgtcaatgt tcccgttaaa tttccaactt tgcaactaca agaagacagc     1020
attcacctac acagcaattg aaaatccaca ccgaagattg acctttgtac aacggtgcta     1080
gaaaccgcgt cactagtaat aactattgga ttgagacatg cacttaacag taaggccccc     1140
aactaatata aaaaccagtt attgggtgtg ttactcatca gcaactacaa cgtgagaaac     1200
```

<210> SEQ ID NO 27
<211> LENGTH: 1309
<212> TYPE: DNA
<213> ORGANISM: Artificial Sequence
<220> FEATURE:
<223> OTHER INFORMATION: Chimeric CaMV35S-ZmPrp sequence

<400> SEQUENCE: 27

```
ggtccgatgt gagactttc aacaaagggt aatatccgga aacctcctcg gattccattg       60
cccagctatc tgtcacttta ttgtgaagat agtggaaaag gaaggtggct cctacaaatg      120
ccatcattgc gataaaggaa aggccatcgt tgaagatgcc tctgccgaca gtggtcccaa      180
agatggaccc ccacccacga ggagcatcgt ggaaaagaa gacgttccaa ccacgtcttc       240
aaagcaagtg gattgatgtg atggtccgat tgagactttt caacaaaggg taatatccgg      300
aaacctcctc ggattccatt gcccagctat ctgtcacttt attgtgaaga tagtggaaaa      360
ggaaggtggc tcctacaaat gccatcattg cgataaagga aaggccatcg ttgaagatgc      420
ctctgccgac agtggtccca agatggaccc ccacccacg aggagcatcg tggaaaagga       480
agacgttcca accacgtctt caaagcaagt ggattgatgt gatgtcgaca actgatgatg      540
agatgaagat tcgagtcgta cgataagtaa taaccagtaa aaggctcata cttaagcggt      600
gtttggtttt tagttattaa tttttaatcc tctaatttat tttatttag tctataaatt       660 atgaaaaata aaatakagtt ttagttttt attagataat ttagagacta aaatataata      720
aggagatgtt tggtttttag agactaattt ttagtcctta tattatattc tatttactc      780 tttaaattac caaatacgaa aactaaaact ctattatata tttagcaatt tagggattaa     840
ataaaataaa ataataaaac taaaaattag tccatataaa tcaaacaccc tctaaaataa     900
aatgaaagga ctaaaaatta agcttcttct ccgaccaagt ggaccatgca tgcttgcatt     960
gtatcgttca ttcttactgc aaaagcgccc atatagcagc atgcaacctg catccatgt     1020 gctcgagcac gcaagcacgt actcgtagta cttgcatatc tactgatcga ggtgtgcatg    1080
cacagcacga aataaatgca gatcgccaag aggatcaaaa attgaattca gcttgatccg    1140
atccgtctag acggacagcg tggattcgag taatttccca tctacaaaac cggcgcccga    1200
gcatctcctt tgtgaccaat gaataactca tgcgcggttc ctgttcgttc gcgcctataa    1260
aagccatggc gcagcagggt cgatctcctc cactacacac aaacacaca                1309
```

<210> SEQ ID NO 28

```
<211> LENGTH: 28
<212> TYPE: DNA
<213> ORGANISM: Medicago truncatula

<400> SEQUENCE: 28
ggatggacat tgaaatcctt catggatt                                      28

<210> SEQ ID NO 29
<211> LENGTH: 28
<212> TYPE: DNA
<213> ORGANISM: Medicago truncatula

<400> SEQUENCE: 29
catcacatgc aatgggcgag agtgaatt                                      28

<210> SEQ ID NO 30
<211> LENGTH: 27
<212> TYPE: DNA
<213> ORGANISM: Medicago truncatula

<400> SEQUENCE: 30
ggggcaatcc taatcctata tttctaa                                       27

<210> SEQ ID NO 31
<211> LENGTH: 27
<212> TYPE: DNA
<213> ORGANISM: Medicago truncatula

<400> SEQUENCE: 31
ccacatgcta tgaagcttta taatctt                                       27

<210> SEQ ID NO 32
<211> LENGTH: 42
<212> TYPE: DNA
<213> ORGANISM: Artificial Sequence
<220> FEATURE:
<223> OTHER INFORMATION: Synthetic primer

<400> SEQUENCE: 32
gatgcggccg cataactcac aaggactaat aataagagag aa                      42

<210> SEQ ID NO 33
<211> LENGTH: 51
<212> TYPE: DNA
<213> ORGANISM: Artificial Sequence
<220> FEATURE:
<223> OTHER INFORMATION: Synthetic primer

<400> SEQUENCE: 33
gaccatggtt tttaaagaaa gtagtgtagt ttactatgaa gtcttacact t             51

<210> SEQ ID NO 34
<211> LENGTH: 41
<212> TYPE: DNA
<213> ORGANISM: Artificial Sequence
<220> FEATURE:
<223> OTHER INFORMATION: Synthetic primer

<400> SEQUENCE: 34
aaggaaaaaa gcggccgcgg atgcatgatt cgattacaaa a                       41

<210> SEQ ID NO 35
<211> LENGTH: 31
<212> TYPE: DNA
<213> ORGANISM: Artificial Sequence
```

```
<220> FEATURE:
<223> OTHER INFORMATION: Synthetic primer

<400> SEQUENCE: 35
ccggatccgg tccgatgtga gacttttcaa c                              31

<210> SEQ ID NO 36
<211> LENGTH: 31
<212> TYPE: DNA
<213> ORGANISM: Artificial Sequence
<220> FEATURE:
<223> OTHER INFORMATION: Synthetic primer

<400> SEQUENCE: 36
ggagatctat cacatcaatc cacttgcttt g                              31

<210> SEQ ID NO 37
<211> LENGTH: 31
<212> TYPE: DNA
<213> ORGANISM: Artificial Sequence
<220> FEATURE:
<223> OTHER INFORMATION: Synthetic primer

<400> SEQUENCE: 37
ccggatccaa ttctcagtcc aaagcctcaa c                              31

<210> SEQ ID NO 38
<211> LENGTH: 32
<212> TYPE: DNA
<213> ORGANISM: Artificial Sequence
<220> FEATURE:
<223> OTHER INFORMATION: Synthetic primer

<400> SEQUENCE: 38
ggagatctaa ttcttttgtg gtcgtcactg cg                             32

<210> SEQ ID NO 39
<211> LENGTH: 28
<212> TYPE: DNA
<213> ORGANISM: Artificial Sequence
<220> FEATURE:
<223> OTHER INFORMATION: Synthetic primer

<400> SEQUENCE: 39
tgatcacctg tcgtacagta tttctaca                                  28

<210> SEQ ID NO 40
<211> LENGTH: 22
<212> TYPE: DNA
<213> ORGANISM: Artificial Sequence
<220> FEATURE:
<223> OTHER INFORMATION: Synthetic primer

<400> SEQUENCE: 40
agccagtgct tgttttgttt ga                                        22

<210> SEQ ID NO 41
<211> LENGTH: 21
<212> TYPE: DNA
<213> ORGANISM: Artificial Sequence
<220> FEATURE:
<223> OTHER INFORMATION: Synthetic 6FAM primer sequence

<400> SEQUENCE: 41
tgatgtgtga tttgtgaaga a                                         21
```

<210> SEQ ID NO 42
<211> LENGTH: 61
<212> TYPE: DNA
<213> ORGANISM: Artificial Sequence
<220> FEATURE:
<223> OTHER INFORMATION: Synthetic primer

<400> SEQUENCE: 42

```
gtattatggt aattaattaa ttggcaaaaa caacaatgaa gctaaaattt tatttattga      60
t                                                                     61
```

<210> SEQ ID NO 43
<211> LENGTH: 29
<212> TYPE: DNA
<213> ORGANISM: Artificial Sequence
<220> FEATURE:
<223> OTHER INFORMATION: Synthetic primer

<400> SEQUENCE: 43

```
acggacgcgg aggccttgcg gttaatttc                                        29
```

<210> SEQ ID NO 44
<211> LENGTH: 2496
<212> TYPE: DNA
<213> ORGANISM: Medicago sativa

<400> SEQUENCE: 44

```
cattggaaac tgaaagcgac attcattttg aaacaaattt ttttggctaa agcgacactc      60
attttgaaac ggagggagta ccatttaagt gagttaatgt gatggaaaaa agataaaatg     120
gtaattttaa catacttcgt cccatattaa gtgacacaat tgaccttatc acacatacca    180
atgcacaatt ttgatgttaa ataactttac taatctctta gaaaaaatta taaaaatatg    240
atattttaaa aatactcatt gagacgaatc caacgacatc ttatataata ttatttatct    300
ttatatatta gtgaaaaaat gcagtcaaaa tatattaggt caatagtaca cgttttcaaa    360
tcatacacgt ttctgaaaaa taatggaagt agtaattctt ttaacgtttt tgttgtttta    420
aaaaatacgt cctccaattt tataagcaat ctttgttttt taaattcatt aaataattga    480
tgtatctgaa atataatata agtcatatac gtcacttatt taatgaattt gaaaataaca    540
aaaattgtat agatgtgaac agaagaagta caagataagt atcacccata gagtttttt    600
tcttctcttt attaacaaat aaaacaaaca caaattttag gagatataga taaaaaata    660
tttttcaaaa gtaaacggac tctaatattt gataggaacc gatcgacaac aaaatagaat    720
tatcaatcat gctggaattt aatttgaaga agaaatgcaa acctaaagag aggggggcta    780
agtaatacca tgctggaact tgaacaagaa aaaccatgct ctaagtaact aagtaaggta    840
gtacattaca ccaattgaga taagtacgac acattatgat gattgagtgc tattaaataa    900
atgatgctgt aggagacaca ttattataac tcacaaggac taataataag agagaacgag    960
agtgtacgtc agtgtaggag acacgttatt ataactttt ataaatattt aagctttgat   1020
aataattttg tcgatctata tataagccac taccaattta aaattatata tatatatata   1080
tatatatata tatatataat aattttattt atatttatta cgttgatggt aaaaaaataa   1140
ataaatttg ttaccattta aaagtcataa atatagtaca atccaaccct ttgagaggtt    1200
aatgtgtgtg cggattttct agataaacaa ggtgccattc acgattcttc ttggtgcagc    1260
ttggagaacc ctatcctggg cttgaagat ttacttcttg ttgatgcttc tagagtacag    1320
ctcttaaggc tgtagtctag ttttttttt catccttcta ccaaaaaaaa aaaagtcata    1380
```

```
aatatagttt atacatataa ctttaataaa aataaaaaat ttcatcccta aaaacatagt    1440
agaaatttca taaaaaaaat attgtttata atttacatgc gttagcagta aaaaatggat    1500
aaattgggta tggagtacta gtaattaata aggttcattg gttaaaaaaa ctaaaaaata    1560
atttctctcc tgatttatat gaaatgacat ttttttggaa catgaagggt attgattttt    1620
acaccttttc aaaagccatt caaggatgaa tatagatttt tggggcatca aacacaagaa    1680
tcattagcat aacatgcttt ggaacacaca catgcttaaa ttaatggttg gagtatcaaa    1740
ttttaaaata ttgttgtcaa tacataccc gtcaatcttc ttttttttac ccaataaaca    1800
ttgaaatgtt gcttctttcg ttaagcataa aaacatcaaa gtctagcaaa atgttgtttt    1860
tgcgatgaca catttcatat agtttaaagg atgcatgatt cgattacaaa aacaaaatac    1920
taataattct agcacaaagt ttaaagcaag attataaagc ttcatagcat gtggatattc    1980
atttagaaat ataggattag gattgcccct ttcatcacgg gtctaacagc accacttgtc    2040
actacatgtc aaaaatgtcc tctagtacag caccgctttt tacttgattc cccttgtcca    2100
tgcatgaaaa aaatcaaaac aatatttgga cacacaaact tgcccccact ttccttttc    2160 ttctgcccta gtttgtttga gactcatatt gatcaaattt ggctatgaat tcaaacaaaa    2220
aattcactct acccattgca tgtgtgggc ccacatataa atccatgaag gatttcaatg    2280
tccatccaag tcaatgattc aacatatata acattgaata atttaattcc aatttgcagt    2340
attatgattt agattgattg ctgcaatacg gtccgtgaat gtgatcactc acgagaaaga    2400
ggtatcaaaa tttcaaggta tttttatttat ttttaacaaa taaaatttca aggtcttgtt    2460
caccatataa acctcctcac tcacacccaa ttctct                              2496

<210> SEQ ID NO 45
<211> LENGTH: 278
<212> TYPE: DNA
<213> ORGANISM: Medicago truncatula
<220> FEATURE:
<221> NAME/KEY: misc_feature
<222> LOCATION: (1)..(278)
<223> OTHER INFORMATION: n is a, t, c, or g

<400> SEQUENCE: 45
aattcaacaa aaaattcact ctcgcccatt gcatgtgntg ggacccacat ataaatccat      60
gaaggatttc aatgtccatc caagtcaatg attcaacata taacattgaa taatttaatt    120
ccaatttgca gtattatgat ttagattgat tgctgcaata cggtccgtga atgtaactca    180
cgagaaagag gtatcaaggt atttttatttt attttttaaca aataaaattt caaggtcttg    240
ttcaccatat aaacctcctc actctcactc aattctct                            278

<210> SEQ ID NO 46
<211> LENGTH: 2429
<212> TYPE: DNA
<213> ORGANISM: Medicago truncatula

<400> SEQUENCE: 46
ataactcaca aggactaata ataagagaga acgaaagtgt acgtgagtgt aggagacacg      60
ttattataac atttttataaa tatttaaacg ttgataataa ttttgtcgat ctataaacca    120
ctaccaattc ctagttaaat atataataat ttttattata tttgttagtt gatggtaaaa    180
gatgaatata atttgttact atattttttt ttgacaaaat aatttgttgc tatttaaaat    240
tcataaatat agtctataca tataatttta ataaaaataa aaattcaccc aaaaaaaaat    300
```

```
caaaaatttc ataaaaaaat aagtattgtt tataattcac gagcgttgtc gcagtacaaa    360
aatggataga tggatacccca gtactagtaa ttaatgaagt taattggtaa aatttcactc    420
ttactggtgg ttgatggtag gggtgtttac ggtgcggttt ggttcggttt tgagagaaaa    480
agtcatccaa accgcaagat aaaaaaacat gcggtttgtg taacacccac agctgacgag    540
ggcaggggag tggtcaccgg tgcacaaggc acgccaatgg gcggctcccg acagcttcta    600
gaggaaccga atcacatctg aatgagaggg atcctgaggc cgtgtaggtg tgggactaca    660
tgaatgaagg aatgcttata agaattgttt ggtaatacct atatcaacaa ggtgcatctt    720 cttttttggta ccctattcca taagaactcc acagttaagc gtgcttgact tggagtagtc    780
tttggatggg tgacctaccg ggattcccga taagcatgcg agtgaggaca aaacacgctg    840
aaaagactcg tgttggtttg tagggtcagt cgacaatgct taaagtcgtc tgggatgtta    900
cagtttggtt tggttcggtt ggctttaaaa taaaatccga accaaaccaa accaatatgg    960
tttgggttgt atcggttggt gcggtttttt cgtgacgata cgattttttg tttccaacat   1020
taaaatcaag ataaaaagct gaaacacaat atattttcaa caatgtttta aatttcatca   1080
aacattacaa tttcattttc attacaatgt ttccaacaac ataaaccaaa ttaaaaacgc   1140
ggacaaaaag taatcttatt ttgtaagaaa tgcaaaagac tgagatgttc tcattctcta   1200
aaagttaagt agcacataaa tacatttta aataaaaagc aaataatgaa cttaacaaga   1260 gaaaaaaat atgacatttt ataaaagttt tcattgagtt tctatgagta ttggtcttga   1320
tgacatatgt ttaattaaca ttttcttat gttacggttt ggtttggttt tgtatctatt   1380
tgacagtctc tttgtacttt gagcgacctc tttagtacgc cttatgctaa agaggtgtct   1440
ctcttattgt gaatatatat cattttacct tcttaaaaaa aagttaattg gtaaaaaaaa   1500
aaaaatttct ctcttgattt atatgaaatg acattttttt tggaacatgg agggtattga   1560 ttttttacacc ttttcaaaag ccactcaagg atgaatatag attttttcatg catcaaacac   1620 aagaatcatt agcataacat gctttggaaa acacacacat atacttaaat taatggttgg   1680
agtatcaaat ttaaaaatat tgttgtcaat acataccccg tcaatcctcc ttttttaccc   1740
aataaacatt gaaatgttgc ttctttcgtt aagcataaaa acatcaaagt ctagcaaaat   1800 gttgttttttg cgatgacaca tttcatatag tttaaaggat gcatgattcg attacaaaaa   1860
caaaatacta ataattctag cacaaagttt aaagctaaga ttataaagct tcatagcatg   1920
tggatattca tttagaaata taggattagg attgcccctt tcatcacggg tctaatagca   1980
ccacttgtca ctacatgtta aaaatgtcct ctagtacaac accgcttttt acttgattcc   2040
ccttgtccat gaaaaaatca aacaatattt ggacacaaaa atttgccccc actttccttt   2100
ttcttctgcc ctagtttgtt tgaaaactca tattgatcta atttggctat ggattcaaac   2160
aaaaaattca ctctgcccat tgcatgtgtg ggacccacat atgaatccgt gaaggatttc   2220
aatgtccatc caagtcaatg attcaacata taacattgaa taatttaatt ccaatttgca   2280
gtattatgat ttagattgat tgctgcaata cggtccgtga atgtaactca cgagaaagag   2340
gtatcaaggt atttttatttt atttttttaaca aataaaattt caaggtcttg ttcaccatat   2400
aaacctcctc actctcactc aattctctt                                      2429
```

<210> SEQ ID NO 47
<211> LENGTH: 593
<212> TYPE: DNA
<213> ORGANISM: Medicago truncatula

<400> SEQUENCE: 47

-continued

```
ggatgcatga ttcgattaca aaaacaaaat actaataatt ctagcacaaa gtttaaagct        60
aagattataa agcttcatag catgtggata ttcatttaga aatataggat taggattgcc       120
cctttcatca cgggtctaat agcaccactt gtcactacat gttaaaaatg tcctctagta       180
caacaccgct ttttacttga ttccccttgt ccatgaaaaa atcaaacaat atttggacac       240
aaaaatttgc ccccactttc cttttcttc tgccctagtt tgtttgaaaa ctcatattga        300
tctaatttgg ctatggattc aaacaaaaaa ttcactctgc ccattgcatg tgtgggaccc       360
acatatgaat ccgtgaagga tttcaatgtc catccaagtc aatgattcaa catataacat       420
tgaataattt aattccaatt tgcagtatta tgatttagat tgattgctgc aatacggtcc       480
gtgaatgtaa ctcacgagaa agaggtatca aggtatttta ttttattttt aacaaataaa       540
atttcgaggt cttgttcacc atataaacct cctcactctc actcaattct ctt             593
```

CHIMERIC AND PROLINE RICH PROTEIN PROMOTERS FOR EXPRESSION IN PLANTS

This application claims the priority of U.S. Provisional Application Ser. No. 60/992,605, filed Dec. 5, 2007, the entire disclosure of which is incorporated herein by reference.

BACKGROUND OF THE INVENTION

1. Field of the Invention

The present invention relates to the field of plant molecular biology and plant genetic engineering, and polynucleic acid molecules useful for gene expression in plants. Specifically, the present invention discloses chimeric polynucleic acid molecules that function as promoters in plant cells. The invention further discloses DNA constructs, plant cells and plants comprising said polynucleic acid molecules, and methods of producing and using the same.

2. Description of Related Art

One of the goals of plant genetic engineering is to produce plants with agronomically desirable characteristics or traits. The proper expression of a desirable transgene in a transgenic plant is one way to achieve this goal. Elements having gene regulatory activity, i.e. regulatory elements such as promoters, leaders, introns and transcription termination regions, are non-coding polynucleotide molecules that play an integral part in the overall expression of genes in living cells. Regulatory elements that function in plants are therefore useful for modifying plant phenotypes through the methods of genetic engineering.

Many regulatory elements are available and are useful for providing good overall gene expression. For example, promoters such as the MAS promoter (U.S. Pat. No. 5,955,646), a ubiquitin promoter (U.S. Pat. Nos. 6,528,701; 6,638,766), P-FMV, the promoter from the 35S transcript of the Figwort mosaic virus (U.S. Pat. No. 6,051,753); P-CaMV 35S, the promoter from the 35S RNA transcript of the Cauliflower mosaic virus (U.S. Pat. No. 5,530,196); P-Os Act1, the promoter from the actin 1 gene of *Oryza sativa* (U.S. Pat. No. 5,641,876); and P-nos, the promoter from the nopaline synthase gene of *Agrobacterium tumefaciens* are known to provide gene expression in most or all of the tissues of a plant during most or all of the plant's lifespan. While previous work has provided a number of regulatory elements useful to affect gene expression in transgenic plants, there is still a great need for novel regulatory elements with beneficial expression characteristics. Many previously identified regulatory elements fail to provide the patterns or levels of expression required to fully realize the benefits of expression of selected genes in transgenic crop plants. One example of this is the need for regulatory elements capable of driving gene expression in different types of plant tissues, and either expressed constitutively but selectively in certain tissue or cell types, or during desirable stages of a plants cell or tissue growth and development.

A plant promoter is a key element for directing transgene expression in a plant cell or tissue. The transcription machinery is assembled and transcription is initiated from the promoter DNA molecule. Transcription factors influence the strength and temporal expression of a transcript from a promoter molecule. Accordingly, regions within the promoter molecule function to enhance or repress transcription.

The genetic enhancement of plants and seeds provides significant benefits to society. For example, plants and seeds may be enhanced with a transgene to provide desirable agricultural, biosynthetic, commercial, chemical, insecticidal, industrial, nutritional, or pharmaceutical properties. Despite the availability of many molecular tools, however, the genetic modification of plants and seeds is often constrained by an insufficient or poorly localized expression of the engineered transgene.

It is of immense social, ecological and economic interests to develop plants that have enhanced nutrition, improved resistance to pests, and tolerance to harsh conditions such as drought. Thus, the identification of new regulatory elements (e.g., promoters) that function in various types of plants is useful in developing enhanced varieties of crops. Clearly, there exists a need in the art for new promoter molecules that are capable of expressing heterologous nucleic acid molecules in important crop species. It is disclosed herein that chimeric promoter DNA molecules comprising a viral promoter DNA enhancer region and a promoter DNA region from a plant proline rich protein (Prp) gene provide an unexpected range of promoter strength and tissue enhanced expression in transgenic plants, and in some cases exhibits a pronounced ability to effectively deliver a pesticidal agent to a pest feeding on the transgenic plant, resulting in increased suppression of pest infestation of the transgenic plant compared to expression of the same pesticidal agent from the Prp promoter segment alone or in combination with other viral enhancer segments. These promoter molecules that exhibit constitutive, temporal, developmental, or tissue-specific expression patterns are of great interest in the development of plants that exhibit agronomically desirable traits.

SUMMARY OF THE INVENTION

The present invention describes compositions and methods of use for regulatory promoter molecules comprising a viral DNA enhancer region operably linked to a plant promoter DNA region of a plant proline rich protein gene. In particular, a promoter construct comprising a plant proline rich protein gene promoter is disclosed, and chimeric promoters are also disclosed which comprise a plant virus promoter enhancer segment linked 5' to a plant proline rich protein gene promoter segment.

The present invention includes and provides a polynucleic acid molecule, or a DNA construct, useful for modulating gene expression in plant cells, in a transgenic plant, in a fertile transgenic plant, or in a seed of a fertile transgenic plant, comprising a chimeric promoter polynucleic acid molecule comprising DNA from a plant virus promoter enhancer region molecule operably linked to a DNA molecule comprising a segment of a promoter molecule from a plant proline rich protein gene. The DNA plant cell virus promoter enhancer region or segment is selected from a caulimovirus promoter, for example, Cauliflower mosaic virus (U.S. Pat. No. 5,352,605), Commelina yellow mottle virus promoter (U.S. Pat. No. 6,963,021), Cotton leaf curl (U.S. Pat. No. 6,610,907), Figwort mosaic (U.S. Pat. No. 6,051,753), Mirabilis mosaic (U.S. Pat. No. 6,420,547), Peanut chlorotic streak (U.S. Pat. No. 5,850,019), Strawberry vein banding, Cassava vein mosaic (U.S. Pat. No. 7,053,205); from a promoter enhancer region selected from a badnavirus promoter, sugarcane bacilliform virus promoter (U.S. Pat. No. 6,093,569), rice tungro bacilliform virus promoter (U.S. Pat. No. 5,824,857); a promoter enhancer region selected from a Phycodnavirus group, *Paramecium bursaria* chlorella virus-1 (PBCV-1), and *Paramecium bursaria* Chlorella NC64A viruses (NC64A viruses). In one embodiment of the present invention, a CaMV 35S tandemly duplicated enhancer (SEQ ID NO: 1)

is linked to a segment of a Prp gene promoter molecule, in another embodiment, a FMV 35S enhancer (SEQ ID NO: 2) is linked to a segment of a Prp gene promoter molecule.

In one embodiment, the invention provides DNA regulatory elements isolated from a plant proline rich protein (Prp) gene and useful for constructing chimeric promoter molecules. For example, such regulatory elements include but are not limited to a *Medicago truncatula* (Mt)Prp promoter molecule, segments and variants thereof (e.g. SEQ ID NO: 3, long variant; SEQ ID NO: 4, short variant; SEQ ID NO: 5, long variant with native leader; SEQ ID NO: 6, short variant with native leader; SEQ ID NO: 45, SEQ ID NO: 46 and SEQ ID NO: 47), a *Medicago sativa* (Ms)Prp promoter molecule (e.g. SEQ ID NO: 7, long variant, SEQ ID NO: 8, short variant; and SEQ ID NO:44), a *Nicotiana plumbaginifolia* (Np)Prp promoter molecule (SEQ ID NO: 9), an *Oryza sativa* (Os)Prp promoter molecule (SEQ ID NO: 10 and 11), a *Pisum sativum* (Ps)Prp promoter (SEQ ID NO: 12), an *Arabidopsis thaliana* (At)Prp promoter (SEQ ID NO: 13 and 14), a *Zea mays* (Zm)Prp promoter (SEQ ID NO: 15), and a *Glycine max* (Gm)Prp promoter (SEQ ID NO: 16, 17, 18), and the like. Exemplary chimeric promoter molecules of the present invention include, but are not limited to FMV35S-MtPrp promoter (SEQ ID NO: 19), CaMV35S-MtPrp promoter (SEQ ID NO:20), CaMV35S-OsPrp promoter (SEQ ID NO: 21 and 22), CaMV35S-PsPrp (SEQ ID NO: 23), CaMV35S-GmPrp (SEQ ID NO: 24, 25, and 26), and CaMV35S-ZmPrp (SEQ ID NO: 27)

In another embodiment, the invention provides DNA constructs comprising a plant expression cassette comprising a chimeric promoter molecule of the present invention operably linked to a DNA molecule of agronomic importance. In another embodiment, the invention provides transgenic plants, seeds and processed products thereof comprising a transgene comprising a chimeric promoter molecule of the present invention. The transgenic plant and progeny thereof preferably provides an agronomically desirable and/or useful phenotype. Agronomically desirable and/or useful phenotypes include but are not limited to herbicide tolerance, insect control, modified yield, fungal disease resistance, virus resistance, plant parasitic nematode resistance, plant pathogenic bacterial disease resistance, plant growth and development, starch production, modified oils production, high oil production, modified fatty acid content, high protein production, fruit ripening, enhanced properties for animal and human nutrition, biopolymers, environmental stress resistance, pharmaceutical peptides and secretable peptides, improved processing traits, improved digestibility, enzyme production, flavor, nitrogen fixation, hybrid seed production, fiber production, cold tolerance, heat and drought stress resistance, increased vigor, increased photosynthetic capacity, increased standability, and biofuel production.

The present invention includes and provides a method of transforming a plant cell with a polynucleic acid molecule comprising a) constructing a recombinant polynucleic acid molecule comprising a DNA plant virus promoter enhancer region operably linked to a plant Prp promoter molecule, which is operably linked to a polynucleic acid molecule of agronomic importance, b) transforming the plant cell with the recombinant polynucleic acid molecule, and c) regenerating said plant cell into a stably transformed transgenic plant. The plant in one embodiment of the invention will be transformed with a polynucleic acid molecule comprising a promoter selected from the group consisting of a sequence as set forth at SEQ ID NOs: 19-27 and at SEQ ID NOs: 44-47.

The present invention provides a method for controlling a plant pest comprising planting seeds of a transgenic crop plant transformed with an expression cassette comprising a chimeric polynucleotide promoter molecule comprising a viral enhancer segment operably linked to a plant Prp promoter segment that provides enhanced expression of a molecule, that when expressed in a plants' cells, confers upon the plant one or more agronomically desirable and/or useful phenotypes, i.e., expression results in the synthesis of one or more molecules exhibiting agronomic importance. In one embodiment, the molecule of agronomic importance is an agent that exhibits pest control when present in the transgenic crop plant and plant cells. More preferably, the pest control agent is a pesticidal protein such as a nematicidal, insecticidal, or fungicidal protein, or is a dsRNA molecule that exhibits a predilection for suppression of one or more target genes in a target pest such as a nematode, an insect, or a fungal cell.

DETAILED DESCRIPTION OF THE INVENTION

Figure 1:
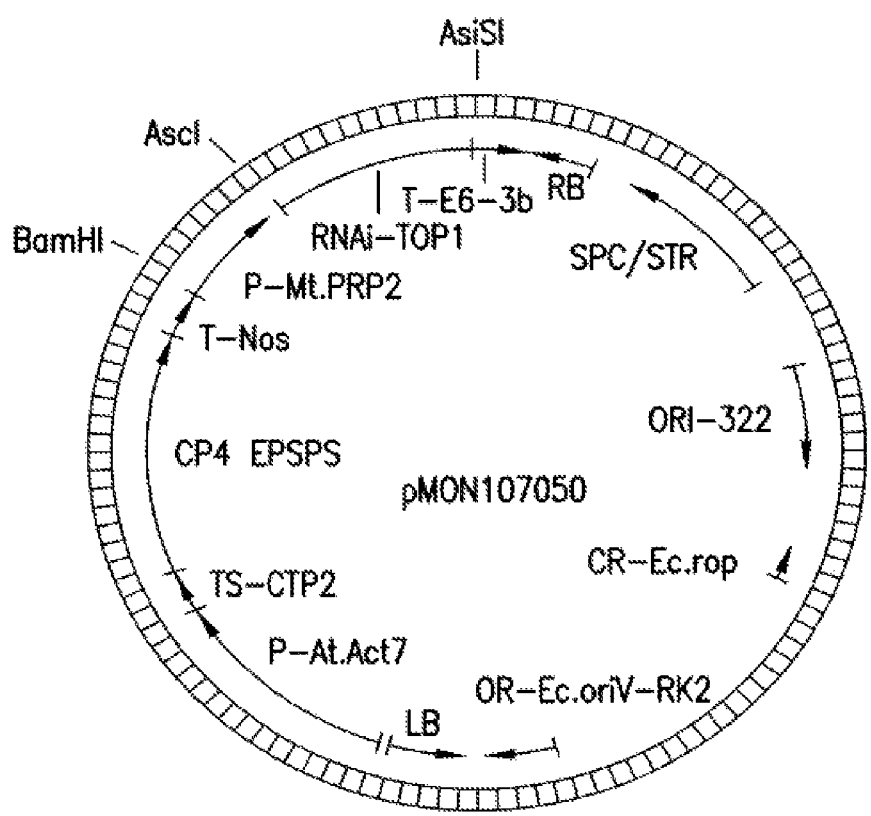
FIG. 1. Diagrammatic representation of plasmid pMON107050.

The invention disclosed herein provides polynucleotide molecules having gene regulatory activity identified from a proline rich protein gene. Such polynucleotide molecules are typically genetically engineered to comprise an operably linked heterologous enhancer region isolated from a plant virus promoter. The design, construction, and use of these polynucleotide molecules are one object of this invention. The exemplary chimeric polynucleotide sequences of these polynucleotide molecules are provided as SEQ ID NO: 19-27. These polynucleotide molecules are capable of affecting the expression of an operably linked transcribable polynucleotide molecule in plant tissues and therefore can selectively regulate gene expression in transgenic plants. The present invention also provides methods of modifying, producing, and using the same. The invention also includes compositions, transformed host cells, transgenic plants, and seeds containing the promoters, and methods for preparing and using the same.

The present invention describes the identification of a plant proline rich protein promoter derived from a *Medicago* species, and more specifically a *Medicago truncatula* or *Medicago sativa* and describes the features of this promoter. The promoter has been shown to exhibit a variety of properties for plant expression. One of the properties described herein is the identification of a segment of the MtPrp promoter that exhibits preferential expression of any linked heterologous sequence in the roots of soybean plants. In addition, it was determined that the level of expression of linked coding sequences or other desirable nucleotide sequences intended for expression in plants, when expressed from the MtPrp promoter segment in soybean roots, was less than desirable. Therefore, based on prior literature in the plant promoter art (for example, U.S. Pat. No. 6,660,911), it was determined that plant viral promoter enhancer sequences could be useful to enhance transgene expression when linked upstream of the MtPrp promoter segment, leading to an increase in the level of expression of desirable molecules of agronomic importance, which confer upon a plant expressing such molecules, one or more agronomically desirable and/or useful phenotypes. Not only did the mating of plant viral promoter enhancer segments to the 5' end of the MtPrp promoter segment result in substantially increased levels of expression of desirable molecules of agronomic importance, but surprisingly, differential tissue and cell expression is observed as well. Tables 1-2 list expression elements and corresponding SEQ ID NOs. comprising sequences from proline rich protein genes, described further below.

TABLE 1

Native proline rich protein (PRP and PRP2) promoters.

| SEQ ID | bp | Expression Element | Annotation |
|---|---|---|---|
| 3 | 2429 | P-Mt.PRP2-1:1:7 | *Medicago truncatula* PRP2 promoter |
| 4 | 593 | P-Mt.PRP2-1:1:8 | *Medicago truncatula* PRP2 promoter |
| 5 | 2472 | PL-Mt.PRP2-1:1:3 | *Medicago truncatula* PRP2 promoter + leader |
| 6 | 636 | PL-Mt.PRP2-1:1:5 | *Medicago truncatula* PRP2 promoter + leader |
| 7 | 2714 | P-MEDsa.PRP2-1:1:1 | *Medicago sativa* PRP2 promoter |
| 8 | 608 | P-MEDsa.PRP2-1:1:2 | *Medicago sativa* PRP2 promoter |
| 9 | 1229 | P-Nt.PRP | *Nicotiana tabacum* PRP promoter |
| 10 | 690 | PL-Os.PRP2-1:1:1 | *Oryza sativa* PRP promoter + leader |
| 11 | 1256 | PL-Os.PRP2-1:1:2 | *Oryza sativa* PRP promoter + leader |
| 12 | 943 | P-Ps.PRP2-1:1:1 | *Pisum sativum* PRP promoter |
| 13 | 925 | P-At.PRP-1 | *Arabidopsis thaliana* PRP promoter |
| 14 | 1052 | P-At.PRP-2 | *Arabidopsis thaliana* PRP promoter |
| 15 | 780 | P-Zm.PRP | *Zea mays* PRP promoter |
| 16 | 1125 | Soy-PRP-PRO:1:1 | *Glycine max* PRP promoter |
| 17 | 1273 | PL-Gm.PRP:1:1 | *Glycine max* PRP promoter |
| 18 | 671 | P-Gm.PRP:1:1 | *Glycine max* PRP promoter |
| 44 | 2496 | P-MEDsa.PRP2-1:1:7 | *Medicago sativa* PRP2 promoter |
| 45 | 278 | P-Mt.PRP2-Bifx-1:1:1 | *Medicago truncatula* PRP2 promoter |
| 46 | 2429 | P-Mt.PRP2-1:1:3 | *Medicago truncatula* PRP2 promoter |
| 47 | 593 | P-Mt.PRP2-1:1:5 | *Medicago truncatula* PRP2 promoter |

TABLE 2

Chimeric promoters comprising proline rich protein promoters.

| SEQ ID | bp | Chimeric Expression Element | Comprises SEQ ID NOs: |
|---|---|---|---|
| 19 | 1049 | FMV35S + MtPRP | 2, 4 |
| 20 | 1165 | CaMV35S + MtPRP | 1, 4 |
| 21 | 1219 | CaMV35S + OsPRP | 1, 10 |
| 22 | 1786 | CaMV35S + OsPRP | 1, 11 |
| 23 | 1472 | CaMV35S + PsPRP | 1, 12 |
| 24 | 1654 | CaMV35S + GmPRP | 1, 16 |
| 25 | 1802 | CaMV35S + GmPRP | 1, 17 |
| 26 | 1200 | CaMV35S + GmPRP | 1, 18 |
| 27 | 1309 | CaMV35S + ZmPRP | 1, 15 |

Polynucleotide Molecules

The following definitions and methods are provided to better define the present invention and to guide those of ordinary skill in the art in the practice of the present invention. Unless otherwise noted, terms are to be interpreted according to conventional usage by those of ordinary skill in the relevant art.

"Proline rich proteins (Prp)" are among the major protein components of plant cell walls, proline-rich proteins that include hydroxy-proline rich glycoproteins (HRGPs) and repetitive proline-rich proteins (RPRPs) and extensins. Many Prp coding sequences have been identified from dicot, monocot and gymnosperm plants, and regulatory molecules have been isolated from Prp genes that include promoter, intron, leader, and 3'UTR molecules, such as, for example, a sugarcane (*Saccharum* species) Prp promoter (U.S. Pat. No. 7,141,427) and an alfalfa (*Medicago sativa*) MsPrp promoter (U.S. Pat. No. 6,936,708). The expression of proline rich proteins from their native promoters may be in response to establishment of disease, wounding, or is otherwise developmentally regulated.

The phrases "coding sequence," "structural sequence," and "transcribable polynucleotide sequence" refer to a physical structure comprising an orderly and contiguous linear arrangement of nucleic acids. The coding sequence and structural sequence nucleic acids are arranged in a series of nucleic acid triplets that each form a codon when viewed within a particular reading frame along the length of the contiguous linear arrangement of nucleic acids. Each codon encodes for a specific amino acid. Thus the coding and structural polynucleotide sequences encode a series of amino acids forming a protein, polypeptide, or peptide sequence. The coding and structural polynucleotide sequences may be contained, without limitation, within a larger nucleic acid molecule, vector, etc. In addition, the orderly arrangement of nucleic acids in these sequences may be depicted, without limitation, in the form of a sequence listing, figure, table, electronic medium, and the like. Transcribable nucleic acid molecules also fit this general description, however, these can also be dsRNA, miRNA, tRNA, rRNA, and catalytic RNA molecules and the like.

As used herein, the term "polynucleotide molecule or polynucleic acid molecule" refers to the single- or double-stranded DNA or RNA molecule of genomic or synthetic origin, i.e., a polymer of deoxyribonucleotide or ribonucleotide bases, respectively, read from the 5' (upstream) end to the 3' (downstream) end.

As used herein, the term "polynucleotide sequence" refers to the sequence of a polynucleotide molecule. The nomenclature for nucleotide bases as used herein can be found in Part 1 of Title 37 of the United States Code of Federal Regulations, in particular at section 1.822, is used herein.

As used herein, the term "regulatory element" refers to a polynucleotide molecule having gene regulatory activity, i.e. one that has the ability to affect the transcription or translation of an operably linked transcribable polynucleotide molecule. Regulatory elements such as promoters, leaders, introns, and transcription termination regions are polynucleotide molecules having gene regulatory activity which play an integral part in the overall expression of genes in living cells. Isolated regulatory elements that function in plants are therefore useful for modifying plant phenotypes through the methods of genetic engineering. By "regulatory element" it is intended a series of nucleotides that determines if, when, and at what level a particular gene is expressed. The regulatory DNA sequences specifically interact with regulatory proteins or other proteins.

As used herein, the term "operably linked or linked" refers to a first polynucleotide molecule joined to a second polynucleotide wherein the polynucleotide molecules are so arranged that the first polynucleotide molecule affects the function of the second polynucleotide molecule. The two polynucleotide molecules may be part of a single contiguous polynucleotide molecule but may be separated by some various length of nucleotides or the two molecules may be adjacent. For example, a plant virus promoter enhancer segment is operably linked to a promoter if the enhancer modulates the expression of a gene of interest from the promoter compared to the construct in the absence of the viral promoter segment, and a promoter is operably linked to a gene of interest if the promoter modulates transcription of the linked gene of interest in a particular cell.

As used herein, the term "gene regulatory activity" refers to a first polynucleotide molecule capable of affecting transcription or translation of an operably linked second polynucleotide molecule. An isolated first polynucleotide molecule having gene regulatory activity may provide temporal, spatial, or developmentally timed expression, or may modulate levels and rates of expression of the operably linked second polynucleotide molecule. An isolated first polynucleotide molecule having gene regulatory activity may comprise a promoter, intron, leader, or 3' transcriptional termination region, and may also comprise expression enhancer elements known to exist within plant virus promoters.

As used herein, the term "gene expression" or "expression" refers to the transcription of a DNA molecule into a transcribed RNA molecule. Gene expression may be described as related to temporal, spatial, developmental, or morphological qualities as well as quantitative or qualitative indications. The transcribed RNA molecule may be translated to produce a protein molecule or may provide an antisense or other regulatory RNA molecule, such as a dsRNA, a tRNA, a rRNA, a miRNA, and the like.

As used herein, an "expression pattern" is any pattern of differential gene expression. In a preferred embodiment, an expression pattern is selected from the group consisting of tissue, temporal, spatial, developmental, stress, environmental, physiological, pathological, cell cycle, and chemically responsive expression patterns.

As used herein, the term "transcribable polynucleotide molecule" refers to any polynucleotide molecule capable of being transcribed into a RNA molecule, including but not limited to protein coding sequences and sequences useful for gene suppression. A "transgene" comprises a DNA molecule heterologous to a host cell.

Determination of Sequence Similarity Using Hybridization Techniques

Nucleic acid hybridization is a technique well known to those of skill in the art of DNA manipulation. The hybridization properties of a given pair of nucleic acids are an indication of their similarity or identity.

The term "hybridization" refers generally to the ability of nucleic acid molecules to join or bind together via complementary base strand pairing. Such hybridization may occur when nucleic acid molecules are contacted under appropriate conditions. "Specifically hybridizes" refers to the ability of two nucleic acid molecules to form an anti-parallel, double-stranded nucleic acid structure. A nucleic acid molecule is said to be the "complement" of another nucleic acid molecule if they exhibit "complete complementarity," i.e., each nucleotide in one molecule is complementary to its base pairing partner nucleotide in another molecule. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Nucleic acid molecules that hybridize to one another, e.g., at least under low stringency conditions are said to be "hybridizable cognates" of each other. Conventional low stringency and high stringency conditions are described herein and by Sambrook et al., (1989) and by Haymes et al., Nucleic Acid Hybridization, A Practical Approach, IRL Press, Washington, D.C. (1985), herein referred to as Sambrook et al., 1989. Departures from complete complementarity are permissible, as long as such departures do not completely preclude the capacity of the molecules to form a double-stranded structure.

Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989). High stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5× Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. High stringency conditions are preferably provided by 6×SSC, 5× Denhardt's solution, 100 mg/mL fish sperm DNA, and 0.1% (w/v) SDS, with an incubation at 55° C. for several hours. Hybridization is generally followed by several wash steps. The wash compositions generally comprise 0.5× to about 10×SSC, and 0.01% (w/v) to about 0.5% (w/v) SDS with a 15 minute incubation at about 20° C. to about 70° C. Preferably, the nucleic acid segments remain hybridized after washing at least one time in 0.1×SSC at 65° C.

A chimeric promoter polynucleic acid molecule of the present invention preferably comprises a plant Prp promoter polynucleic acid sequence that hybridizes, under low or high stringency conditions, with SEQ ID NO: 3 through SEQ ID NO: 6, any complements thereof, or any fragments thereof, or any cis elements thereof; SEQ ID NO: 7 or 8, any complements thereof, or any fragments thereof, or any cis elements thereof; SEQ ID NO: 9 through 18, any complements thereof, or any fragments thereof, or any cis elements thereof, or SEQ ID NO: 19-27, complements thereof, or any fragments thereof, or any cis elements thereof.

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *Journal of Molecular Biology* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Advances in Applied Mathematics,* 2:482-489, 1981, Smith et al., *Nucleic Acids Research* 11:2205-2220, 1983). The percent identity is most preferably determined using the "Best Fit" program.

Useful methods for determining sequence identity are also disclosed in Guide to Huge Computers, Martin J. Bishop, ed., Academic Press, San Diego, 1994, and Carillo, H., and Lipton, D., *Applied Math* (1988) 48:1073. More particularly, preferred computer programs for determining sequence identity include the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., *J. Mol. Biol.* 215:403-410 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the invention is a polynucleotide molecule that has at least from about 70% sequence identity to at least from about 99%-100%, or any percentage point in between, sequence identity with a polynucleotide sequence described herein. Polynucleotide molecules and variants thereof that are capable of regulating transcription of operably linked transcribable polynucleotide molecules and have a substantial percent sequence identity to the polynucleotide sequences of the polynucleotide molecules provided herein are encompassed within the scope of this invention.

"Homology" refers to the level of similarity between two or more nucleic acid or amino acid sequences in terms of percent of positional identity (i.e., sequence similarity or identity). Homology also refers to the concept of similar functional properties among different nucleic acids or proteins.

For purposes of this invention "percent identity" may also be determined using BLASTX version 2.0 for translated nucleotide sequences and BLASTN version 2.0 for polynucleotide sequences. In a preferred embodiment of the present invention, the presently disclosed corn genomic promoter sequences comprise nucleic acid molecules or fragments having a BLAST score of more than 200, preferably a BLAST score of more than 300, and even more preferably a BLAST score of more than 400 with their respective homologues.

Polynucleotide Molecules, Motifs, Fragments, Chimeric Molecules, Enhancers

Enhancers activate transcription, frequently in a specific differentiated cell type or tissue. Although enhancers often lie within a few kilobases of the cap site, in some cases they lie much further upstream or downstream from the cap site or within an intron. Some genes are controlled by more than one enhancer region, as in the case of the *Drosophila* even-skipped gene.

As used herein, the term "enhancer domain" refers to a cis-acting transcriptional regulatory element (cis-element), which confers an aspect of the overall modulation of gene expression of a linked sequence, which, when expressed, comprises a molecule of agronomic importance. An enhancer domain may function to bind transcription factors, which are trans-acting protein factors that regulate transcription. Some enhancer domains bind more than one transcription factor, and transcription factors may interact with different affinities with more than one enhancer domain. Enhancer domains can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from regulatory elements that include such elements, and they can be synthesized with additional flanking nucleotides that contain useful restriction enzyme sites to facilitate subsequence manipulation. Any of the polynucleotide molecules of the present invention may comprise an enhancer.

Chimeric promoter molecules of the present invention combine a viral promoter enhancer molecule and a plant Prp promoter molecule that confers or modulates gene expression from the promoter, by fusing a viral promoter enhancer domain from a first viral promoter to a second Prp gene promoter with its own partial or complete regulatory elements. Examples of suitable promoter enhancer molecule to be used in the practice of the present invention include, but are not limited to the enhancer molecules from promoters such as P-FMV, the promoter from the 35S transcript of the Figwort mosaic virus (described in U.S. Pat. No. 6,051,753) and P-CaMV 35S, the promoter from the 35S RNA transcript of the Cauliflower mosaic virus (described in U.S. Pat. Nos. 5,530,196, 5,424,200, and 5,164,316). The DNA plant cell virus promoter enhancer region is selected from a caulimovirus promoter, for example, from Blueberry Red Ringspot virus, Cauliflower Mosaic Virus (U.S. Pat. No. 5,352,605), Carnation etched ring Virus, Commelina yellow mottle Virus promoter, Cotton Leaf Curl (U.S. Pat. No. 6,610,907 Dahlia Mosaic, Figwort Mosaic (U.S. Pat. No. 6,051,753), Horseradish Latent, Mirabilis Mosaic (U.S. Pat. No. 6,420,547), Peanut Chlorotic Streak (U.S. Pat. No. 5,850,019), Soybean Chlorotic Mottle, Strawberry Vein Banding, Thistle Mottle, Aquilegia Necrotic Mosaic, Cassava Vein Mosaic (U.S. Pat. No. 7,053,205), Cestrum virus, Petunia Vein Clearing, Plantago Virus 4, or Sonchus Mottle; a promoter enhancer region is selected from a badnavirus promoter, for example, Sugarcane Bacilliform Virus promoter (U.S. Pat. No. 6,093,569), Rice Tungro Bacilliform Virus promoter (U.S. Pat. No. 5,824,857); a promoter enhancer region is selected from a Phycodnavirus group, *Paramecium bursaria* Chlorella virus-1 (PBCV-1), and *Paramecium bursaria* Chlorella NC64A viruses (NC64A viruses). The construction of chimeric promoters using viral promoter enhancer domains is described in, for example, U.S. Pat. No. 6,660,911, to enhance an agronomically important trait.

Reference to a segment of a polynucleotide molecule, segment of a promoter sequence, or segment of a viral promoter or viral promoter enhancer sequence, is intended to encompass any length of a functional fraction of the nucleotide sequence that confers its regulatory properties upon a linked sequence. The segment can consist of the full length of, for example, the viral promoter including any enhancer element, the viral enhancer element, and any combination or multiplicity of such elements. A segment of a PRP promoter as set forth herein can comprise any length of a PRP promoter so long as transcription of a gene of interest can be facilitated by linking the gene of interest to the segment of a PRP promoter.

The invention disclosed herein provides polynucleotide molecules comprising regulatory element fragments that may be used in constructing novel chimeric regulatory elements. Novel combinations comprising fragments of these polynucleotide molecules and at least one other regulatory element or fragment can be constructed and tested in plants and are considered to be within the scope of this invention. Thus, the design, construction, and use of chimeric regulatory elements is one object of this invention. As used herein, the term "fragment" or "fragment thereof" refers to a polynucleotide sequence length that comprises at least 25, at least 50, at least 75, at least 85, or at least 95 contiguous nucleotide bases wherein its complete sequence is in its entirety identical to a contiguous component of the referenced polynucleotide molecule.

Promoters

Among the gene expression regulatory elements, the promoter plays a central role. The transcription machinery is assembled and transcription is initiated along the promoter molecule. This early step is often rate-limiting relative to subsequent stages of protein production. Transcription initiation at the promoter may be regulated in several ways. For example, a promoter may be induced by the presence of a particular compound or external stimuli, express a gene only in a specific tissue, express a gene during a specific stage of development, or constitutively express a gene. Thus, transcription of a transgene may be regulated by operably linking the coding sequence to promoters with different regulatory characteristics. Accordingly, a regulatory element such as promoters, play a pivotal role in enhancing the agronomic, pharmaceutical or nutritional value of crops.

As used herein, the term "promoter" refers to a polynucleotide molecule that is involved in recognition and binding of RNA polymerase II and other proteins such as transcription factors (trans-acting protein factors that regulate transcription) to initiate transcription of an operably linked gene. A promoter may be isolated from the 5' untranslated region (5' UTR) of a genomic segment comprising an expressed sequence. Alternately, a promoter molecule may be artificially and/or synthetically produced or comprise a modified DNA sequence. Promoters may be defined by their temporal, spatial, or developmental expression pattern in a particular cell or tissue type. A promoter can be used as a regulatory element for modulating expression of an operably linked transcribable polynucleotide molecule. Promoters may themselves contain sub-elements such as cis-elements or enhancer domains that effect the transcription of operably linked transcribable polynucleotide molecules. A "plant promoter" is a native or non-native promoter that is functional in plant cells. A plant promoter can be used as a 5' regulatory element for modulating expression of an operably linked gene or genes. A plant promoter of the present invention includes an isolated genomic DNA region located 5' to a DNA coding sequence of a plant proline rich protein or extensin protein. Any plant proline rich protein gene promoter can be isolated and combined with a plant viral promoter enhancer to create a chimeric promoter molecule, and the chimeric promoter can be tested in transformed plant cells or plants as described in the present invention to select the chimeric promoter that provides a desirable enhanced expression level or change in tissue expression pattern.

Many regulatory elements act in cis ("cis elements") and are believed to affect DNA topology, producing local conformations that selectively allow or restrict access of RNA polymerase to the DNA template or that facilitate selective opening of the double helix at the site of transcriptional initiation. Cis elements occur within the 5' UTR associated with a particular coding sequence, and are often found within promoters and promoter modulating sequences (inducible elements). Cis elements can be identified using known cis elements as a target sequence or target motif in the BLAST programs of the present invention. Examples of cis-acting elements in the 5'UTR associated with a polynucleotide coding sequence include, but are not limited to, promoters and enhancers.

Promoters of the present invention can include between about 300 bp (base pair) upstream and about 10 kb (kilobase) upstream of the trinucleotide ATG sequence at the translational start site of a protein coding region. Promoters of the present invention can preferably include between about 300 bp upstream and about 5 kb upstream of the trinucleotide ATG sequence at the translational start site of a protein coding region. Promoters of the present invention can more preferably include between about 300 bp upstream and about 2 kb upstream of the trinucleotide ATG sequence at the translational start site of a protein coding region. Promoters of the present invention can include between about 300 bp upstream and about 1 kb upstream of the trinucleotide ATG sequence at the start site of a protein coding region. While in many circumstances a 300 bp promoter may be sufficient for expression, additional sequences may act to further regulate expression, for example, in response to biochemical, developmental or environmental signals.

The chimeric promoter comprises polynucleic acid segments or variants thereof that exhibit at least from about 85% to about 99%-100% identity to a polynucleic acid segment, or any portion in between, as provided in any of the promoter sequences as set forth at SEQ ID NO: 1-27 and SEQ ID NOs:44-47.

At least two types of information are useful in predicting promoter regions within a genomic DNA sequence. First, promoters may be identified on the basis of their sequence "content," such as transcription factor binding sites and various known promoter motifs. (Stormo, *Genome Research* 10: 394-397, 2000). Such signals may be identified by computer programs that identify sites associated with promoters, such as TATA boxes and transcription factor (TF) binding sites. Second, promoters may be identified on the basis of their "location," i.e. their proximity to a known or suspected coding sequence (Stormo). Promoters are typically found within a region of DNA extending approximately 150-1500 basepairs in the 5' direction from the translational start codon of a coding sequence. Thus, promoter regions may be identified by locating the translational start codon of a coding sequence, and moving beyond the start codon in the 5' direction to locate the promoter region.

Promoter sequence may be analyzed for the presence of common promoter sequence characteristics, such as a TATA-box and other known transcription factor binding site motifs. These motifs are not always found in every known promoter, nor are they necessary for every promoter to function, but when present, do indicate that a segment of DNA is a promoter sequence.

For identification of the TATA-box, the putative promoter sequences immediately upstream of the transcription start site of the predicted genes within a given sequence size range, as described above, are used. The transcription start site and TATA-box (if present) may be predicted with program TSSP. TSSP is designed for predicting PolII promoter regions in plants, and is based on the discriminate analysis combing characteristics of functional elements of regulatory sequence with the regulatory motifs from Softberry Inc.'s plant RegSite database (Solovyev V. V. (2001) *Statistical approaches in Eukaryotic gene prediction*. In: Handbook of Statistical genetics (eds. Balding D. et al.), John Wiley & Sons, Ltd., p. 83-127). In the cases in which multiple TATA-boxes are predicted, only the rightmost (closest to the 5' end of the translation initiation codon) TATA-box is retained. The transcription start sites (TSS) are refined and extended upstream, based on the matches to the database sequences. Promoter sequences with unique TATA-box, as well the TATA-box locations, may be identified within the promoter sequences.

For identification of other known transcription factor binding motifs (such as a GC-box, CAAT-box, etc.), the promoter sequences immediately upstream of the translation start site of the predicted genes within a given sequence size range, as described above, are used. The known transcription factor binding motifs (except TATA-box) on the promoter sequences are predicted with a proprietary program PromoterScan. The identification of such motifs provides important information about the candidate promoter. For example, some motifs are associated with informative annotations such as (but not limited to) "light inducible binding site" or "stress inducible binding motif" and can be used to select with confidence a promoter that is able to confer light inducibility or stress inducibility to an operably-linked transgene sequence desired to be expressed under such regulatory conditions.

The activity or strength of a promoter may be measured in terms of the amount of mRNA tRNA, dsRNA, miRNA, rRNA, or protein is specifically accumulated during a particular period of time in the growth of a tissue or cell or cell type containing the transgene.

Regulatory Element Isolation and Modification

Any number of methods well known to those skilled in the art can be used to isolate a polynucleotide molecule, or fragment thereof, disclosed in the present invention. For example, PCR (polymerase chain reaction) technology can be used to amplify flanking regions from a particular starting nucleotide sequence. A number of methods are known to those of skill in the art to amplify unknown polynucleotide molecules adjacent to a core region of known polynucleotide sequence. Methods include but are not limited to inverse PCR (IPCR), vectorette PCR, Y-shaped PCR, and genome walking approaches. Polynucleotide fragments can also be obtained by other techniques such as by directly synthesizing the fragment by chemical means, as is commonly practiced by using an automated oligonucleotide synthesizer. For the present invention, the polynucleotide molecules were isolated from genomic plant DNA by designing oligonucleotide primers based on available sequence information and using PCR techniques to extract a particular segment of DNA.

As used herein, the term "isolated polynucleotide molecule" refers to a polynucleotide molecule at least partially separated from other molecules normally associated with it in its native state. In one embodiment, the term "isolated" is also used herein in reference to a polynucleotide molecule that is at least partially separated from nucleic acids which normally flank the polynucleotide in its native state. Thus, polynucleotides fused to regulatory or coding sequences with which they are not normally associated, for example as the result of recombinant techniques, are considered isolated herein. Such molecules are considered isolated even when present, for example in the chromosome of a host cell, or in a nucleic acid solution. The term "isolated" as used herein is intended to encompass molecules not present in their native state.

Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

Short nucleic acid sequences having the ability to specifically hybridize to complementary nucleic acid sequences may be produced and utilized in the present invention. These short nucleic acid molecules may be used as probes to identify the presence of a complementary nucleic acid sequence in a given sample. Thus, by constructing a nucleic acid probe which is complementary to a small portion of a particular nucleic acid sequence, the presence of that nucleic acid sequence may be detected and assessed. Use of these probes may greatly facilitate the identification of transgenic plants which contain the presently disclosed nucleic acid molecules. The probes may also be used to screen cDNA or genomic libraries for additional nucleic acid sequences related or sharing homology to the presently disclosed promoters and transcribable polynucleotide sequences. The short nucleic acid sequences may be used as probes and specifically as PCR probes. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3, STSPipeline, or GeneUp (Pesole, et al., *BioTechniques* 25:112-123, 1998), for example, can be used to identify potential PCR primers.

Alternatively, the short nucleic acid sequences may be used as oligonucleotide primers to amplify or mutate a complementary nucleic acid sequence using PCR technology. These primers may also facilitate the amplification of related complementary nucleic acid sequences (e.g. related nucleic acid sequences from other species).

The primer or probe is generally complementary to a portion of a nucleic acid sequence that is to be identified, amplified, or mutated. The primer or probe should be of sufficient length to form a stable and sequence-specific duplex molecule with its complement. The primer or probe preferably is about 10 to about 200 nucleotides long, more preferably is about 10 to about 100 nucleotides long, even more preferably is about 10 to about 50 nucleotides long, and most preferably is about 14 to about 30 nucleotides long. The primer or probe may be prepared by direct chemical synthesis, by PCR (for example, U.S. Pat. Nos. 4,683,195, and 4,683,202), or by excising the nucleic acid specific fragment from a larger nucleic acid molecule.

Regulatory Elements in a DNA Construct

Various regulatory sequences may be included in a recombinant DNA construct. Any such regulatory sequences may be provided in a recombinant vector with other regulatory sequences. Such combinations can be designed or modified to produce desirable regulatory features. Constructs of the present invention would typically comprise one or more gene expression regulatory elements operably linked to a transcribable polynucleotide molecule operably linked to a 3' transcription termination polynucleotide molecule.

As used herein, the term "leader" refers to a polynucleotide molecule isolated from the untranslated 5' region (5' UTR) of a genomic copy of a gene and defined generally as a segment between the transcription start site (TSS) and the coding sequence start site. Alternately, leaders may be synthetically produced or manipulated DNA elements. A "plant leader" is a native or non-native leader that is functional in plant cells. A plant leader can be used as a 5' regulatory element for modulating expression of an operably linked transcribable polynucleotide molecule. For example, non-translated 5' leader polynucleotide molecules derived from heat shock protein genes have been demonstrated to enhance gene expression in plants (see for example, U.S. Pat. Nos. 5,659,122 and 5,362,865). Chimeric promoter molecules of the present invention may optionally comprise a native leader polynucleotide molecule linked to a plant Prp promoter segment for which it is naturally found. This molecule can be replaced as necessary with a heterologous leader molecule.

As used herein, the term "intron" refers to a polynucleotide molecule that may be isolated or identified from the intervening sequence of a genomic copy of a gene and may be defined generally as a region spliced out during mRNA processing prior to translation. Alternately, introns may be synthetically produced or manipulated DNA elements. Introns may themselves contain sub-elements such as cis-elements or enhancer domains that effect the transcription of operably linked genes. A "plant intron" is a native or non-native intron that is functional in plant cells. A plant intron may be used as a regulatory element for modulating expression of an operably linked gene or genes. A polynucleotide molecule sequence in a recombinant construct may comprise introns. The introns may be heterologous with respect to the transcribable polynucleotide molecule sequence.

The transcribable polynucleotide molecule sequence in the recombinant vector may comprise introns. The introns may be heterologous with respect to the transcribable polynucleotide molecule sequence. Examples of regulatory element introns include the rice actin intron (U.S. Pat. No. 5,641,876) and the corn HSP70 intron (U.S. Pat. No. 5,859,347).

The 3' untranslated regions (3' UTRs) of mRNAs are generated by specific cleavage and polyadenylation. A 3' polyadenylation region means a DNA molecule linked to and located downstream of a structural polynucleotide molecule and includes polynucleotides that provide a polyadenylation signal and other regulatory signals capable of affecting transcription, mRNA processing or gene expression. PolyA tails are thought to function in mRNA stability and in initiation of translation. Examples of 3' UTR regions are the nopaline synthase 3' region (nos 3'; Fraley, et al., *Proc. Natl. Acad. Sci.* USA 80: 4803-4807, 1983), wheat hsp17 (T-Ta.Hsp17), and T-Ps.RbcS2:E9 (pea rubisco small subunit) cotton E6 (U.S. Pat. No. 6,096,950) and those disclosed in WO0011200A2 and other 3' UTRs known in the art can be tested and used in combination with a transcribable polynucleic acid molecule, for example the coixin terminator (U.S. Pat. No. 6,635,806).

Constructs and vectors may also include a transit peptide coding sequence that expresses a linked peptide that is useful for targeting of a protein product, particularly to a chloroplast, leucoplast or other plastid organelle, or mitochondria, or peroxisome, or vacuole or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of other such isolated chloroplast proteins include, but are not limited to those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS) and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide, such as, the *Arabidopsis thaliana* EPSPS CTP (CTP2, Klee et al., *Mol. Gen. Genet.* 210:437-442), and the *Petunia hybrida* EPSPS CTP (CTP4, della-Cioppa et al.,

*Proc. Natl. Acad. Sci. USA* 83:6873-6877) has been show to target heterologous EPSPS protein sequences to chloroplasts in transgenic plants. The production of glyphosate tolerant plants by expression of a fusion protein comprising an amino-terminal CTP with a glyphosate resistant EPSPS enzyme is well known by those skilled in the art, (U.S. Pat. Nos. 5,627,061, 5,633,435, 5,312,910, EP 0218571, EP 189707, EP 508909, and EP 924299).

DNA Constructs

The DNA constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permit the integration of the T-DNA into the genome of a plant cell (see for example U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art, see for example, Molecular Cloning: A Laboratory Manual, 3rd edition Volumes 1, 2, and 3 (2000) J. F. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908, 4,940,835, 4,769,061 and 4,757,011. These types of vectors have also been reviewed (Rodriguez, et al., Vectors: A Survey of Molecular Cloning Vectors and Their Uses, Butterworths, Boston, 1988; Glick et al., Methods in Plant Molecular Biology and Biotechnology, CRC Press, Boca Raton, Fla., 1993). Typical vectors useful for expression of nucleic acids in higher plants are well known in the art and include vectors derived from the tumor-inducing (Ti) plasmid of *Agrobacterium tumefaciens* (Rogers, et al., *Meth. In Enzymol*, 153: 253-277, 1987). Other recombinant vectors useful for plant transformation, including the pCaMVCN transfer control vector, have also been described (Fromm et al., *Proc. Natl. Acad. Sci. USA*, 82: 5824-5828, 1985).

Transcribable Polynucleotide Molecules

A promoter or chimeric promoter molecule of the present invention may be operably linked to a transcribable polynucleotide sequence that is heterologous with respect to the promoter molecule. The term "heterologous" refers to the relationship between two or more polynucleic acid or protein sequences that are derived from different sources. For example, a promoter is heterologous with respect to a transcribable polynucleotide sequence if such a combination is not normally found in nature. In addition, a particular sequence may be "heterologous" with respect to a cell or organism into which it is inserted (i.e. does not naturally occur in that particular cell or organism).

The transcribable polynucleotide molecule may generally be any polynucleic acid sequence for which an increased level or differential cell or tissue expression of a transcript is desired. Alternatively, the regulatory element and transcribable polynucleotide sequence may be designed to down-regulate a specific polynucleic acid sequence. This is typically accomplished by linking the promoter to a transcribable polynucleotide molecule that is oriented in the antisense direction. One of ordinary skill in the art is familiar with such antisense technology. Briefly, as the antisense polynucleic acid molecule is transcribed, it hybridizes to and sequesters a complimentary polynucleic acid molecule inside the cell. This duplex RNA molecule cannot be translated into a protein by the cell's translational machinery and is degraded in the cell. Any polynucleic acid molecule may be negatively regulated in this manner.

A regulatory element of the present invention may also be operably linked to a modified transcribable polynucleotide molecule that is heterologous with respect to the promoter. The transcribable polynucleotide molecule may be modified to provide various desirable features. For example, a transcribable polynucleotide molecule may be modified to increase the content of essential amino acids, enhance translation of the amino acid sequence, alter post-translational modifications (e.g., phosphorylation sites), transport a translated product to a compartment inside or outside of the cell, improve protein stability, insert or delete cell signaling motifs, etc.

Due to the degeneracy of the genetic code, different nucleotide codons may be used to code for a particular amino acid. A host cell often displays a preferred pattern of codon usage. Transcribable polynucleotide molecules are preferably constructed to utilize the codon usage pattern of the particular host cell. This generally enhances the expression of the transcribable polynucleotide molecule in a transformed host cell. Any of the above described polynucleic acid and amino acid molecules may be modified to reflect the preferred codon usage of a host cell or organism in which they are contained. Modification of a transcribable polynucleotide molecule for optimal codon usage in plants is described, for example, in U.S. Pat. No. 5,689,052.

Additional variations in the transcribable polynucleotide molecules may encode proteins having equivalent or superior characteristics when compared to the proteins from which they are engineered. Mutations may include, but are not limited to, deletions, insertions, truncations, substitutions, fusions, shuffling of motif sequences, and the like. Mutations to a transcribable polynucleotide molecule may be introduced in either a specific or random manner, both of which are well known to those of skill in the art of molecular biology.

Thus, one embodiment of the invention is a chimeric promoter molecule of the present invention, such as provided in SEQ ID NO: 19-27 or variant thereof, operably linked to a transcribable polynucleotide molecule so as to modulate transcription of the transcribable polynucleotide molecule at a desired level or in a desired tissue or developmental pattern upon introduction of said construct into a plant cell. In one embodiment, the transcribable polynucleotide molecule comprises a protein-coding region of a gene, and the chimeric promoter molecule affects the transcription of a functional mRNA molecule that is translated and expressed as a protein product. In another embodiment, the transcribable polynucleotide molecule comprises an antisense region of a gene, and the regulatory element affects the transcription of an antisense RNA molecule or other similar inhibitory RNA in order to inhibit expression of a specific RNA molecule of interest in a target host cell.

Genes of Agronomic Interest

The transcribable polynucleotide molecule preferably encodes a polypeptide that is suitable for incorporation into the diet of a human or an animal. Specifically, such transcribable polynucleotide molecules comprise genes of agronomic interest. As used herein, the term "gene of agronomic interest" refers to a transcribable polynucleotide molecule that includes but is not limited to a DNA coding sequence or other element intended for expression in the plant cell, and when expressed in a particular plant tissue, cell, or cell type provides a desirable characteristic associated with plant morphology, physiology, growth and development, exhibiting an effect upon the yield of the plant or plant product, nutritional enhancement, disease or pest resistance, or environmental or chemical tolerance. Suitable transcribable polynucleotide molecules include but are not limited to those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, or a pesticidal protein, or any other agent such as a dsRNA molecule targeting a particular gene for suppression either within the plant in order to cause an effect upon the plant physiology or metabolism or to be provided as a pesticidal agent in the diet of a pest that feeds on the plant.

In one embodiment of the invention, a polynucleotide molecule as shown in SEQ ID NO: 19-27 or SEQ ID NOs:44-47, or variants thereof, is incorporated into a construct such that the polynucleotide molecule of the present invention is operably linked to a transcribable polynucleotide molecule that is a gene of agronomic interest.

The expression of a gene of agronomic interest is desirable in order to confer an agronomically important trait. A gene of agronomic interest (a transcribable polynucleotide molecule) that provides a beneficial agronomic trait to crop plants may be, for example, including, but not limited to genetic elements comprising herbicide resistance (U.S. Pat. Nos. 6,803,501; 6,448,476; 6,248,876; 6,225,114; 6,107,549; 5,866,775; 5,804,425; 5,633,435; 5,463,175), increased yield (U.S. Pat. USRE38,446; 6,716,474; 6,663,906; 6,476,295; 6,441,277; 6,423,828; 6,399,330; 6,372,211; 6,235,971; 6,222,098; 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; 6,506,962), virus resistance (U.S. Pat. Nos. 6,617,496; 6,608,241; 6,015,940; 6,013,864; 5,850,023; 5,304,730), nematode resistance (U.S. Pat. No. 6,228,992), bacterial disease resistance (U.S. Pat. No. 5,516,671), plant growth and development (U.S. Pat. Nos. 6,723,897; 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; 6,380,462), high oil production (U.S. Pat. Nos. 6,495,739; 5,608,149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; 6,171,640), biopolymers (U.S. Pat. USRE37,543; 6,228,623; 5,958,745 and U.S. Patent Publication No. US20030028917), environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700). The genetic elements, methods, and transgenes described in the patents listed above are incorporated herein by reference and include but are not limited to herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production.

Alternatively, a transcribable polynucleotide molecule can effect the above mentioned plant characteristic or phenotype by encoding a RNA molecule that causes the targeted inhibition of expression of an endogenous gene, for example via antisense, inhibitory RNA (RNAi), or co-suppression-mediated mechanisms. The RNA could also be a catalytic RNA molecule (i.e., a ribozyme) engineered to cleave a desired endogenous mRNA product. Thus, any transcribable polynucleotide molecule that encodes a transcribed RNA molecule that affects an agronomically important phenotype or morphology change of interest may be useful for the practice of the present invention.

Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829; post-transcriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Application Publication 20070124836) and compositions isolated from nematode pests (U.S. Patent Application Publication 20070250947).

Plant pests include, but are not limited to arthropod pests, nematode pests, and fungal or microbial pests. Important arthropods plant pest families include Acarina, Coleoptera, Diptera, Hemiptera, Homoptera, Hymenoptera, Lepidoptera, Orthoptera, and Thysanoptera. Agronomically important soil inhabiting insects include, but are not limited to *Diabroticina, Diaprepes, Pachnaeus, Asynonuchus, Lycoriella, Sciara, Stenophlus*, and *Bradysia* among others. There are numerous plant-parasitic nematode species, including various cyst nematodes (e.g. *Heterodera* spp.), root knot nematodes (e.g. *Meloidogyne* spp.), lesion nematodes (e.g. *Pratylenchus* spp.), dagger nematodes (e.g. *Xiphinema* spp.) and stem and bulb nematodes (e.g. *Ditylenchus* spp.), among others. Tylenchid nematodes (members of the order Tylenchida), including the families Heteroderidae, Meloidogynidae, and Pratylenchidae, are the largest and most economically important group of plant-parasitic nematodes. Other important plant-parasitic nematodes include Dorylaimid nematodes (e.g. *Xiphinema* spp.), among others. Other plant pests include fungi, bacteria, mycoplasmas and viruses. Fungal plant pathogens include obligate parasites (Uredinales, Ustilaginales, Erysiphales, and Oomycetes), facultative parasites, and facultative saprophytes, which include, but are not limited to the following: Ascomycete fungi such as of the genera *Venturia, Podosphaera, Erysiphe, Monilinia, Mycosphaerella*, and *Uncinula*; Basidiomycete fungi such as from the genera *Hemileia, Rhizoctonia*, and *Puccinia*; Fungi imperfecti such as the genera *Botrytis, Helminthosporium, Rhynchosporium, Fusarium* (e.g., *F. moniliforme*), *Septoria, Cercospora, Alternaria, Pyricularia*, and *Pseudocercosporella* (e.g., *P. herpotrichoides*); Oomycete fungi such as from the genera *Phytophthora* (e.g., *P. parasitica. P. medicaginis, P. megasperma*), *Peronospora* (e.g., *P. tabacina*), *Bremia, Pythium*, and *Plasmopara*; as well as other fungi such as *Sclerophthora macrospora, Sclerophthora rayissiae, Sclerospora graminicola, Peronosclerospora sorghi, Peronosclerospora philippinensis, Peronosclerospora sacchari, Peronosclerospora maydis, Physopella zeae, Cercospora zeae-maydis, Colletotrichum graminicola, Gibberella zeae, Exserohilum turcicum, Kabatiellu zeae*, and *Bipolaris maydis*; and bacteria such as *Pseudomonas* species, for example, *Pseudomonas syringae, Pseudomonas tabaci; Xanthomonas* species, *Erwinia* species and *Corynebacterium* species; and mycoplasma, mycoplasma-like, rickettsia and rickettsia-like organisms, for example the causal agents of Pierce's disease, Alfalfa Dwarf, Phony Peach disease, Aster Yellows disease, Peach X-disease, corn stunt, and Peach Yellow disease. Particularly preferred pathogens include, but are not limited to: *Puccinia, Rhizoctonia*, GGT, stripe rust, Asian soybean rust (*Phakopsora pachyrhizi*), *Fusarium* species, *Verticillium* species, gray leaf spot, *Phytophthora* species and corn rust. Agronomically important plant viruses include but are not limited to Potyviruses, Luteoviruses, Geminiviruses, Ilarviruses, Comoviruses, Caulimoviruses, Cucumoviruses, Fijiviruses, Alfamoviruses, Badnaviruses, Bromoviruses, Furoviruses, Tospoviruses, Tobamoviruses, for example, soybean mosaic virus, bean pod mottle virus, cotton leaf curl virus, potato leaf roll virus, barley yellow dwarf virus, potato virus Y, tomato yellow leaf curl virus, maize dwarf mosaic virus, cucumber mosaic virus, tomato mosaic virus, tomato spotted wilt virus, and watermelon mosaic virus.

Exemplary transcribable polynucleotide molecules for incorporation into constructs of the present invention include, for example, polynucleotide molecules or genes from a species other than the target species or genes that originate with or are present in the same species, but are incorporated into recipient cells by genetic engineering methods rather than classical reproduction or breeding techniques. The type of polynucleotide molecule can include but is not limited to a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding B-glucuronidase (GUS described in U.S. Pat. No. 5,599,670, which is incorporated herein by reference), green fluorescent protein and variants thereof (GFP described in U.S. Pat. Nos. 5,491,084 and 6,146,826, RFP and the like), proteins that confer antibiotic resistance, or proteins that confer herbicide tolerance. Marker genes in genetically modified plants are generally of two types: genes conferring antibiotic resistance or genes conferring herbicide tolerance.

Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art.

Herbicides for which transgenic plant tolerance has been demonstrated and the method of the present invention can be applied, include but are not limited to: amino-methyl-phosphonic acid, glyphosate, glufosinate, sulfonylureas, imidazolinones, bromoxynil, dalapon, dicamba, cyclohexanedione, protoporphyrinogen oxidase inhibitors, and isoxaflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSPS described in U.S. Pat. Nos. 5,627,061, 5,633,435, 6,040,497 and in 5,094,945 for glyphosate tolerance); polynucleotides encoding a glyphosate oxidoreductase and a glyphosate-N-acetyl transferase (GOX described in U.S. Pat. No. 5,463,175 and GAT described in U.S. Patent publication 20030083480, dicamba monooxygenase U.S. Patent publication 20030135879); a polynucleotide molecule encoding bromoxynil nitrilase (Bxn described in U.S. Pat. No. 4,810,648 for Bromoxynil tolerance); a polynucleotide molecule encoding phytoene desaturase (crtI) described in Misawa et al, 1993 (*Plant J.* 4:833-840); and Misawa et al., 1994 (*Plant J.* 6:481-489) for norflurazon tolerance; a polynucleotide molecule encoding acetohydroxyacid synthase (AHAS, aka ALS) described in Sathasiivan et al. (1990) (*Nucl. Acids Res.* 18:2188-2193) for tolerance to sulfonylurea herbicides; and the bar gene described in DeBlock, et al. (1987) (*EMBO J.* 6:2513-2519) for glufosinate and bialaphos tolerance. The chimeric promoter molecules of the present invention can express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, glyphosate oxidoreductase and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable marker genes will be apparent to those of skill in the art.

The selectable marker is preferably GUS, green fluorescent protein (GFP) or variants thereof, neomycin phosphotransferase II (nptII), luciferase (LUX), an antibiotic resistance protein, or a herbicide (e.g., glyphosate, bromoxynil, and the like) resistance or tolerance protein. The selectable marker is most preferably a kanamycin, hygromycin, or herbicide resistance marker.

Cell Transformation

The invention is also directed to a method of producing transformed cells and plants which comprise, in a 5' to 3' orientation, a Mt.PRP2 promoter, or a chimeric promoter operably linked to a heterologous transcribable polynucleotide molecule. Other molecules may also be introduced into the cell, including 3' transcriptional terminators, 3' polyadenylation signals, other translated or untranslated sequences, transit or targeting sequences, selectable markers, enhancers, and operators. Preferably the chimeric promoter comprises a plant viral promoter enhancer segment linked 5' to a plant PRP or PRP2 promoter segment such as a segment consisting of a nucleotide sequence as set forth herein as SEQ ID NO:4, SEQ ID NO:5, and SEQ ID NO:6.

The term "transformation" refers to the introduction of nucleic acid into a recipient host. The term "host" refers to bacteria cells, fungi, animals and animal cells, plants and plant cells, or any plant parts or tissues including protoplasts, calli, roots, tubers, seeds, stems, leaves, seedlings, embryos, and pollen. As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. The term "transgenic" refers to an animal, plant, or other organism containing one or more heterologous polynucleic acid molecules.

There are many methods for introducing heterologous polynucleic acid molecules into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.*, 42: 205, 1991).

Technology for introduction of a transgene DNA molecule into cells is well known to those of skill in the art. Methods and materials for transforming plant cells by introducing a plant polynucleotide construct into a plant genome in the practice of this invention can include any of the well-known and demonstrated methods including but not limited to:

chemical methods (Graham and Van der Eb, *Virology*, 54: 536-539, 1973; Zatloukal, et al., *Ann. N.Y. Acad. Sci.*, 660:136-153, 1992);

physical methods such as microinjection (Capecchi, *Cell*, 22:479-488, 1980), electroporation (Wong and Neumann, *Biochim. Biophys. Res. Commun.*, 107:584-587, 1982; Fromm et al., *Proc. Natl. Acad. Sci. USA*, 82:5824-5828, 1985; U.S. Pat. No. 5,384,253) particle acceleration (Johnston and Tang, *Methods Cell Biol.*, 43(A):353-365, 1994; Fynan et al., *Proc. Natl. Acad. Sci. USA*, 90:11478-11482, 1993) and microprojectile bombardment (as illustrated in U.S. Pat. Nos. 5,015,580; 5,550,318; 5,538,880; 6,160,208; 6,399,861; and 6,403,865);

viral vectors (Clapp, *Clin. Perinatol.*, 20:155-168, 1993; Lu, et al., *J. Exp. Med.*, 178:2089-2096, 1993; Eglitis and Anderson, *Biotechniques*, 6:608-614, 1988);

receptor-mediated mechanisms (Curiel et al., *Hum. Gen. Ther.*, 3:147-154, 1992; Wagner, et al., *Proc. Natl. Acad. Sci. USA*, 89:6099-6103, 1992), and bacterial mediated mechanisms such as *Agrobacterium*-mediated transformation (as illustrated in U.S. Pat. Nos. 5,824,877; 5,591,616; 5,981,840; and 6,384,301);

Nucleic acids can be directly introduced into pollen by directly injecting a plant's reproductive organs (Zhou, et al., *Methods in Enzymology*, 101:433, 1983; Hess, *Intern Rev. Cytol.*, 107:367, 1987; Luo, et al., *Plant Mol Biol. Reporter*, 6:165, 1988; Pena, et al., *Nature*, 325:274, 1987); and Protoplast transformation, as illustrated in U.S. Pat. No. 5,508,184.

The nucleic acids may also be injected into immature embryos (Neuhaus, et al., *Theor. Appl. Genet.*, 75:30, 1987).

Any of the above described methods may be utilized to transform a host cell with one or more gene regulatory elements of the present invention and one or more transcribable polynucleotide molecules. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Methods for transforming dicotyledonous plants, primarily by use of *Agrobacterium tumefaciens* and obtaining transgenic plants have been published for cotton (U.S. Pat. Nos. 5,004,863; 5,159,135; 5,518,908); soybean (U.S. Pat. Nos. 5,569,834; 5,416,011; McCabe, et al., *Biotechnology*, 6:923, 1988; Christou et al., *Plant Physiol.* 87:671-674

(1988)); *Brassica* (U.S. Pat. No. 5,463,174); peanut (Cheng et al., *Plant Cell Rep.* 15:653-657 (1996), McKently et al., *Plant Cell Rep.* 14:699-703 (1995)); papaya; and pea (Grant et al., *Plant Cell Rep.* 15:254-258 (1995)).

Transformation of monocotyledon plants using electroporation, particle bombardment and *Agrobacterium* have also been reported. Transformation and plant regeneration have been achieved in asparagus (Bytebier et al., *Proc. Natl. Acad. Sci. (USA)* 84:5354 (1987)); barley (Wan and Lemaux, *Plant Physiol* 104:37 (1994)); maize (Rhodes et al., *Science* 240:204 (1988); Gordon-Kamm et al., *Plant Cell* 2:603-618 (1990); Fromm et al., *Bio/Technology* 8:833 (1990); Koziel et al., *Bio/Technology* 11:194 (1993); Armstrong et al., *Crop Science* 35:550-557 (1995)); oat (Somers et al., *Bio/Technology* 10:1589 (1992)); orchard grass (Horn et al., *Plant Cell Rep.* 7:469 (1988)); corn (Toriyama et al., *Theor Appl. Genet.* 205:34 (1986); Part et al., *Plant Mol. Biol.* 32:1135-1148 (1996); Abedinia et al., *Aust. J. Plant Physiol.* 24:133-141 (1997); Zhang and Wu, *Theor. Appl. Genet.* 76:835 (1988); Zhang et al., *Plant Cell Rep.* 7:379 (1988); Battraw and Hall, *Plant Sci.* 86:191-202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)) and wheat (Vasil et al., *Bio/Technology* 10:667 (1992); U.S. Pat. No. 5,631,152).

The regeneration, development, and cultivation of plants from transformed plant protoplast or explants is well taught in the art (Weissbach and Weissbach, *Methods for Plant Molecular Biology*, (Eds.), Academic Press, Inc., San Diego, Calif., 1988; Horsch et al., *Science,* 227:1229-1231, 1985). In this method, transformed cells are generally cultured in the presence of a selective media, which selects for the successfully transformed cells and induces the regeneration of plant shoots and roots into intact plants (Fraley et al., *Proc. Natl. Acad. Sci. U.S.A.,* 80: 4803, 1983). These plants are typically obtained within two to four months.

The regenerated transgenic plants are self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books (Allard, "Principles of Plant Breeding," John Wiley & Sons, NY, U. of CA, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, *In: Soybeans: Improvement, Production and Uses,* 2nd Edition, *Manograph.,* 16:249, 1987; Fehr, "Principles of variety development," *Theory and Technique*, (Vol. 1) and *Crop Species Soybean* (Vol. 2), Iowa State Univ., Macmillan Pub. Co., NY, 360-376, 1987). Conversely, pollen from non-transgenic plants may be used to pollinate the regenerated transgenic plants.

The transformed plants are analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used transgene expression. Primer sets (pairs of DNA molecules that specifically hybridize to a target polynucleotide molecule) are developed to identify specific transcribed transgene sequences. For example, the expression of transcript of the present invention can be identified and measured in the sample using DNA primer molecules SEQ ID NO: 39, 40 and 6FAM primer SEQ ID NO: 41 in the TaqMan® assay or SEQ ID NO: 42 and 43 in the Invader® assay that are specific for identification of the E6 termination sequence (U.S. Pat. No. 6,096,950) of the transgene expression cassette described in the present invention, other primer molecules can be selected by those skilled in the art from DNA sequences disclosed herein or other DNA sequences comprising any transgene transcript from which the expression is driving by a chimeric promoter molecule of the present invention that measures the presence or expression levels of the transgene transcripts.

The seeds of the plants of this invention can be harvested from fertile transgenic plants and be used to grow progeny generations of transformed plants of this invention including hybrid plant lines comprising the construct of this invention and expressing a gene of agronomic interest. The present invention also provides for parts of the plants of the present invention. Plant parts, without limitation, include seed, endosperm, ovule and pollen. In a particularly preferred embodiment of the present invention, the plant part is a seed. The invention also includes and provides transformed plant cells which comprise a nucleic acid molecule of the present invention.

The transgenic plant may pass along the transgenic polynucleic acid molecule to its progeny. Progeny includes any regenerable plant part or seed comprising the transgene derived from an ancestor plant. The transgenic plant is preferably homozygous for the transformed polynucleic acid molecule and transmits that sequence to all of it's offspring upon as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified. Each periodical, patent, and other document or reference cited herein is herein incorporated by reference in its entirety.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

This example provides descriptions of compositions in use or contemplated for use in the present invention singularly or in any combination.

The present invention provides polynucleotide molecules having promoter activity and DNA constructs comprising the promoter molecules operably linked to a transcribable polynucleotide molecule. A crop transformation base vector comprising selection expression cassettes and elements necessary for the maintenance of the plasmid in a bacteria cell is used to assemble DNA segments (promoters, leaders, introns, 3'UTR) that provide regulatory activity when operably linked to DNA segments that provide functionality in the present invention. The assembly of these DNA segments can be accomplished using methods known in the art of recombinant DNA technology. The exemplary DNA chimeric promoter molecules of the present invention, such as any one or more of the DNA molecules identified as SEQ ID NO: 19-27 or variants thereof, are assembled from a DNA segment comprising a promoter enhancer isolated from a plant virus promoter and a DNA segment comprising a promoter isolated from a plant proline rich protein gene.

The *Medicago truncatula* Prp promoter segment is isolated from a genomic library of the plant using GenomeWalker™ (Clonetech, Mountain View, Calif.) and primer molecules SEQ ID NO: 28-29 and 30-31) and the DNA polynucleotide sequence determined. The long version of the MtPrp promoter with leader (SEQ ID NO: 3) is isolated from the genomic DNA segment produced by the GenomeWalker™ reaction using primer molecules SEQ ID NO: 32 and 33. The short version of the MtPrp promoter with leader (SEQ ID NO: 4) is isolated from the genomic segment using primer molecules SEQ ID NO: 33 and 34. Additional variants are created by removing the leader sequences from SEQ ID NO:3 and 4 to create SEQ ID NO: 5 and 6, respectively. The variant promoter molecules are linked to reporter genes and tested in transgenic plants. Additionally, selected variants are used in combination with the viral enhancer segments (SEQ ID NO:1 and 2) to create chimeric promoter molecules.

Other plant Prp promoter molecules useful in the present invention include, but are not limited to a *Medicago sativa* MsPrp promoter molecule (SEQ ID NO:7, long variant and SEQ ID NO:8, short variant), a *Nicotiana plumbaginifolia* NpPrp promoter molecule (SEQ ID NO: 9), an *Oryza sativa* OsPrp promoter molecule (SEQ ID NO:10 and 11), a *Pisum sativum* PsPrp promoter (SEQ ID NO: 12), an *Arabidopsis thaliana* AtPrp promoter (SEQ ID NO: 13 and 14), *Zea mays* ZmPrp promoter (SEQ ID NO:15), and *Glycine max* GmPrp promoter (SEQ ID NO:16, 17, and 18).

The viral enhancer promoter segments are isolated by PCR from base DNA constructs using DNA primer molecules. The DNA construct pMON97752 comprises the CaMV35S promoter with a tandem duplicated enhancer. This construct is used as a DNA template to isolate a 539 bp CaMV35S enhancer segment (SEQ ID NO: 1) using primer molecules SEQ ID NO: 35 and SEQ ID NO:36. The DNA construct pMON101405 comprises the FMV35S promoter. The construct is used as a DNA template to isolate a 423 bp FMV enhancer segment (SEQ ID NO:2) using primer molecules SEQ ID NO:37 and SEQ ID NO:38. The primer molecules included the sequence of a BamH1 restriction enzyme cleavage site at the 5' end and the sequence of a BglII restriction enzyme cleavage site at the 3' end of the enhancer segments to add in the linkage of the enhancer elements to isolated Prp promoter molecules. For example, a viral enhancer segment (FMV35S or CaMV35S) is linked to the 5' end of a MtPRP promoter (SEQ ID NO: 4) by cloning into restriction enzyme sites to form a chimeric FMV35S-MtPRP promoter (SEQ ID NO:19) or CaMV35S-MtPrp (SEQ ID NO:20).

A chimeric promoter of the present invention is constructed by linking a viral promoter enhancer segment to a plant Prp promoter segment. The viral enhancer segments (SEQ ID NO:1 and 2) can be engineered with BamH1 and BglII enzyme restriction sequences and the like to facilitate their linkage with isolated Prp promoter segments. In this example, viral enhancer segments constructed to contain BamH1 and BglII flanking sequences were each linked separately to the 5' end of an MtPrp promoter segment by digestion of pMON107050 (FIG. 1) with BamH1 and ligation with T4 DNA ligase (Roche, Indianapolis, Ind. Cat#11 635 379 001). Selected clones resulting from the cloning were screened with BamH1/Sca1 restriction enzyme digestion and the desired orientation selected. The chimeric promoters, FMV35S-MtPrp (SEQ ID NO:19) and CaMV35S-MtPrp (SEQ ID NO: 20) were constructed in this manner. Additional chimeric promoters can be created by isolation of viral enhancer segments, for example, SEQ ID NO:1 is added to the 5' end of any of SEQ ID NOs:3-18. Exemplary chimeric promoters include, but are not limited to CaMV35S-OsPrp (SEQ ID NO:21), CaMV35S-OsPrp (SEQ ID NO:22), CaMV35S-PsPrp (SEQ ID NO:23), CaMV35S-GmPrp (SEQ ID NO:24), CaMV35S-GmPrp (SEQ ID NO:25), CaMV35S-GmPrp (SEQ ID NO:26), and CaMV35S-ZmPrp (SEQ ID NO:27), or variants thereof.

Promoter molecules of the present invention can be operably linked to a polynucleotide molecule in a DNA construct. For example, a polynucleotide molecule that when transcribed provides a dsRNA that comprises a segment of a *Heterodera glycines* specific topoisomerase coding segment, Top-1 (SEQ ID NO: 1521, and SEQ ID NO: 1298, US Patent Publication No. 20070250947), specifically isolated from a *H. glycines* DNA library. The Top-1 segment was inserted between the MtPrp promoter and an E6 transcription termination segment to construct the plant transformation vector pMON107050 (FIG. 1). The Top-1 segment was also inserted between the chimeric promoters FMV35S-MtPrp or CaMV35S-MtPrp, as the case required, and an E6 transcription termination segment to construct the relevant portion of the plant transformation expression vectors pMON97769 (FIG. 2) and pMON97770 (FIG. 3), which were used to transform soybean cells. Transgenic soybean plants were regenerated from such transformed cells.

Example 2

This example illustrates expression analysis from MtPRP and viral enhanced MtPRP chimeric promoters in stable transformed soy plants.

The *Agrobacterium*-mediated soybean transformation to produce plants comprising the DNA constructs comprising the molecules of the present invention is based on the method described by Martinell et al., which allows the generation of germline transformed plants without utilization of callus (U.S. Pat. No. 6,384,301 and US2005-0005321-A1). Exemplary DNA constructs of the present invention include pMON107050 (short MtPrp/Top-1), pMON97769 (FMV35S-MtPrp/Top-1), pMON97770 (CaMV35S-MtPrp/Top-1), pMON59355 (long MtPrp/GUS), and pMON59354 (short MtPrp/GUS).

Briefly, meristem tissues are excised from the embryos of imbibed soybean A3525 or A3244 (Asgrow®) seed. After co-culturing with the *Agrobacterium* carrying the DNA construct, the meristems are placed on selection medium to inhibit the growth of untransformed plant cells and excess *Agrobacterium*. The meristems are then placed in media conducive to shoot and root development, and only rooted plants with normal phenotypic characteristics are selected and transferred to soil for growth and further assessment. Expression from the transgenes transformed into soybean cells is determined by measuring GUS activity or mRNA levels using a polynucleotide detection method depending on the construct used to transform the soybean cells.

The DNA constructs containing GUS as a scorable marker are analyzed qualitatively and quantitatively measured using methods known to those skilled in the art. Briefly, plant tissue samples are collected from the same tissue for both the qualitative and quantitative assays. For qualitative analysis, whole tissue sections are incubated with the GUS staining solution X-Gluc (5-bromo-4-chloro-3-indolyl-b-glucuronide) (0.4 milligram/milliliter) for an appropriate length of time, rinsed, and visually inspected for blue coloration. Samples are then put into a 50/50 mixture of glacial acetic acid and ethanol and stored overnight at room temperature to allow for clearing of the chlorophyll. Once cleared the samples are stored in 70% ethanol for viewing. For quantitative analysis, total protein is first extracted from each tissue sample. 0.5 to 2 micrograms of total protein is used with the fluorogenic substrate 4-methyleumbelliferyl-b-D-glucuronide (MUG) in a total reaction volume of 50 μl (microliters). The reaction product 4-methlyumbelliferone (4-MU) is maximally fluorescent at high pH. Addition of a basic solution of sodium carbonate simultaneously stops the assay and adjusts the pH for quantifying the fluorescent product. Fluorescence is measured with a Perceptive Biosystems Series 4000 Cytofluor instrument with 360/40 excitation and 460/40 emission filters, with gain set at 80. The GUS activity is expressed as pMole of 4-MU/micrograms of protein/hour (pMole of 4-MU/micrograms/protein/hour).

The results of GUS expression analysis are shown in Table 3 for the pMON59355 construct (MtPrp/GUS, long promoter version with leader, SEQ ID NO: 5). Ten transgenic soybean plants were assayed at each plant stage and various tissues were sampled including a R5 seed cotyledon, seed pod, yellow pod seed embryo, yellow pod seed cotyledon, root, sink leaf and source leaf. Abbreviations include: reproductive stages (R3, R5), yellow pod (mature seed pod), and three leaf stage (V3). Mean levels of GUS activity (pMole of MU/μg protein/hour) for each stage of plant development and organ tested are provided. The results of the analysis show that the immature pod (R3) exhibited the highest expression followed by V3 root. Mature V3 source leaf exhibited the lowest expression levels.

TABLE 3

GUS analysis of soybean tissues transformed with MtPrp/GUS, pMON59355.

| Plant stage | Tissue type | Average | | Std error |
|---|---|---|---|---|
| R5 | Cotyledon | 71.86 | ± | 8.58 |
| R3 | Pod | 484.96 | ± | 69.80 |
| Yellow pod | Embryo | 106.29 | ± | 12.77 |
| Yellow pod | Cotyledon | 99.92 | ± | 9.81 |
| V3 | Root | 146.15 | ± | 32.08 |
| V3 | Sink Leaf | 59.70 | ± | 27.84 |
| V3 | Source Leaf | 11.01 | ± | 0.68 |

The results of GUS expression analysis are shown in Table 4 for the pMON59354 construct (MtPrp/GUS, short promoter version with leader, SEQ ID NO: 6). Ten transgenic soybean plants were assayed at each plant stage and various tissues were sampled including a R5 seed cotyledon, seed pod, yellow pod seed embryo, yellow pod seed cotyledon, root, sink leaf and source leaf. Abbreviations include: reproductive stages (R3, R5), yellow pod (mature seed pod), and three leaf stage (V3). Mean levels of GUS activity (pMole of MU/μg protein/hour) for each stage of plant development and organ tested are provided. The results of the analysis show that the immature pod (R3) exhibited the highest expression followed by V3 root. Mature V3 source leaf exhibited the lowest expression levels. Surprisingly, the short MtPrp promoter version exhibited a higher level of expression in roots and, except in immature pods, a reduced level of expression in other plant tissues, relative to the long version of the promoter.

TABLE 4

GUS analysis of soybean tissues transformed with MtPrp/GUS, pMON59354.

| Plant stage | Tissue type | Average | | Std error |
|---|---|---|---|---|
| R5 | Cotyledon | 35.52 | ± | 434 |
| R3 | Pod | 564.02 | ± | 217.31 |
| Yellow pod | Embryo | 34.03 | ± | 4.26 |
| Yellow pod | Cotyledon | 82.65 | ± | 17.15 |
| V3 | Root | 206.66 | ± | 50.19 |
| V3 | Sink Leaf | 29.22 | ± | 3.18 |
| V3 | Source Leaf | 0.00 | ± | 0.00 |

Figure 2:
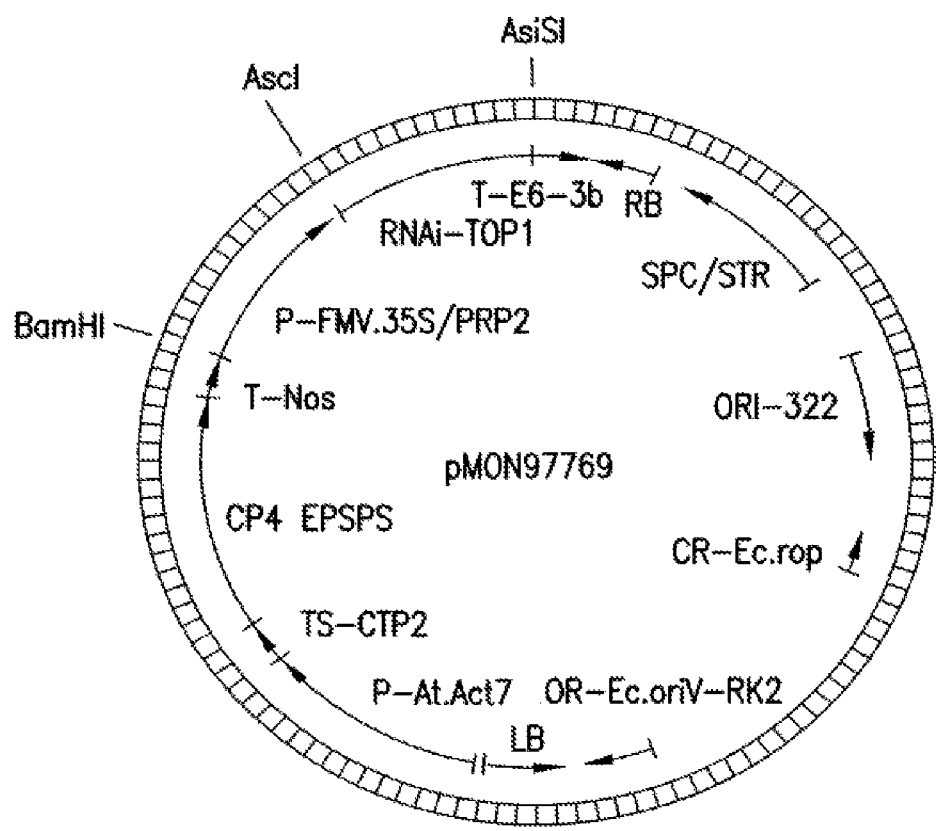
FIG. 2. Diagrammatic representation of plasmid pMON97769.
Figure 3:
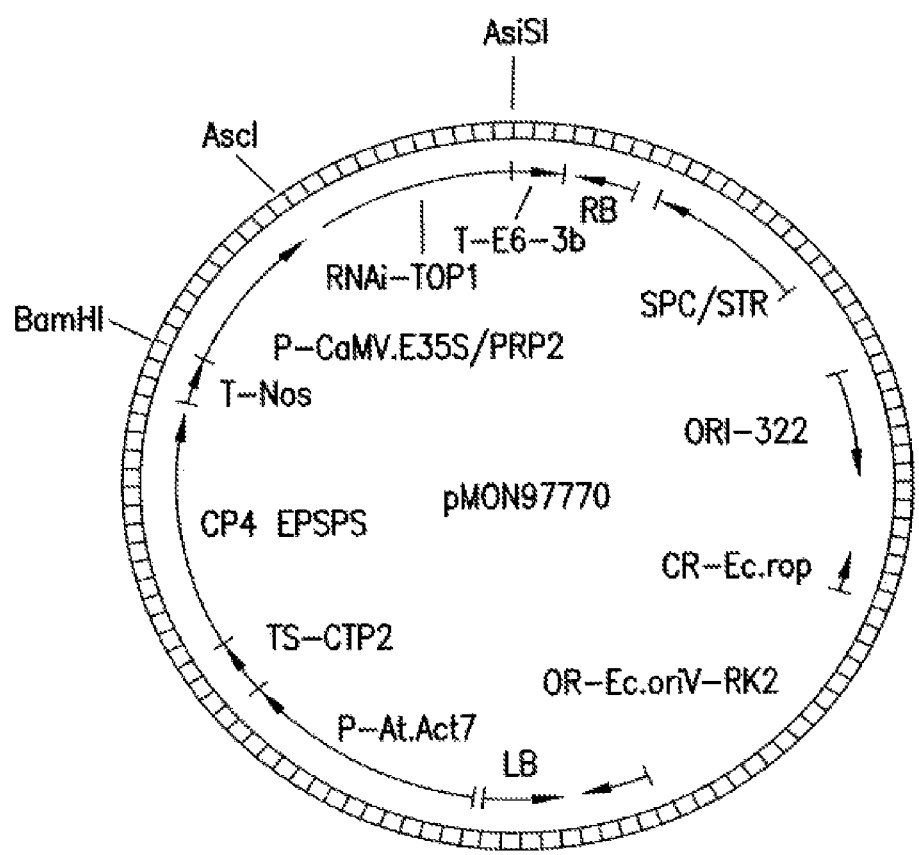
FIG. 3. Diagrammatic representation of plasmid pMON97770.

Detecting or measuring transcription of the recombinant DNA construct in the transgenic plant cell of the invention can be achieved by any suitable method, including protein detection methods (for example, western blots, ELISAs, and other immunochemical methods), measurements of enzymatic activity, or nucleic acid detection methods (for example, Southern blots, northern blots, PCR, RT-PCR, fluorescent in situ hybridization). In particular, the expression of the exemplary DNA constructs of the present invention can be determined by measuring the amount of mRNA produced in root and leaf tissue of transgenic soybean plants that are transformed with a construct such as pMON107050 (FIG. 1, P-MtPrp/Top1/E6, SEQ ID NO:3, MtPrp promoter), pMON97769 (FIG. 2, P-FMV35S-MtPrp/Top1/E6, SEQ ID NO:19, chimeric promoter), and pMON97770 (FIG. 3, P-CaMVe35S-MtPrp/Top1/E6, SEQ ID NO:20, chimeric promoter). The mRNA produced in cells of transgenic plants transformed with these vector constructs were analyzed by Taqman® and Invader® analysis using DNA primer molecules specific for the E6 termination segment of the DNA constructs according to methods provided by the manufacturer. The expression of top1 dsRNA transcript from these cassettes in transgenic plants was identified and measured using DNA primer molecules SEQ ID NOs:39, 40, and 6FAM primer SEQ ID NO:41 in the TaqMan® assay, or using SEQ ID NOs:42, and 43 in the Invader® assay. These primers provide specific identification of the E6 termination sequence in the mRNA transcript. Table 5 shows the results of the mRNA transcript expression analysis from leaf and root samples of transgenic soybean plants transformed with the exemplary DNA constructs. The values are compared to a control transgenic plant sample that does not contain the E6 termination sequence. Plants transformed with the vector pMON107050 expressing top1 from the MtPrp promoter exhibited no detectable mRNA in leaf tissue samples and low levels in root. In contrast, plants transformed with the chimeric promoter constructs exhibited a surprising and dramatic increase in transcript levels in leaf and root samples. Surprisingly, there is a differential tissue expression level between the two chimeric promoter constructs. The P-FMV-MtPrp promoter (pMON97769) provided similar expression levels in leaf and root while the P-CaMV-MtPrp (pMON97770) promoter construct exhibited a seven fold differential between leaf and root expression. When comparing expression of the two chimeric promoters it is apparent that CaMV-MtPrp promoter expresses more strongly in leaf tissue while the FMV-MtPrp promoter expresses more strongly in root tissue. These results demonstrate that expression levels in planta from a plant Prp promoter can be enhanced by the addition of a viral promoter enhancer segment at the 5' end of the PRP promoter segment and that differential tissue expression can be selected depending on the selected viral enhancer.

TABLE 5

Expression analysis of mRNA transcripts in leaf and root tissue.

| DNA construct | Number Transgenic events tested | Leaf average Transcript Level | Leaf Standard error | Root average Transcript Level | Root Standard error |
| --- | --- | --- | --- | --- | --- |
| pMON107050 P-MtPrp | 18 | 0 | 0 | 356 | 93 |
| pMON97769 P-FMV35S-MtPrp | 25 | 22340 | 7292 | 16404 | 4821 |
| pMON97770 P-CaMV35S-MtPrp | 20 | 56442 | 14515 | 8119 | 4058 |

Example 3

This example illustrates specific embodiments in which the promoters of the present invention are particularly useful.

A soybean cyst nematode (*Heterodera glycines*) plant greenhouse pot assay is used to evaluate the resistance of transgenic soybean plants expressing an SCN inhibitory nucleotide sequence to infection by and reproduction of the soybean cyst nematode on roots. Transgenic soybean plants were selected which express a dsRNA for suppression of an essential SCN gene encoding a topoisomerase, top1. Constructs designed to express the SCN inhibitory agent are set forth herein at pMON107050 (FIG. 1, P-MtPrp/Top1/E6, SEQ ID NO:3, MtPrp promoter), pMON97769 (FIG. 2, P-FMV35S-MtPrp/Top1/E6, SEQ ID NO:19, chimeric promoter), and pMON97770 (FIG. 3, P-CaMVe35S-MtPrp/Top1/E6, SEQ ID NO:20, chimeric promoter). Three or four inch diameter square pots are filled with clean sand and watered thoroughly. Transgenic and control soybean seeds (A3525 or A3244, Asgrow®), or alternatively any rooted plant parts, are planted one per pot in the center of the pot and watered well to remove air pockets. The pots are incubated in the greenhouse or growth chamber at 20° C. to 30° C. until the plants reached a suitable age for inoculation. Soybeans started from seed are typically inoculated 2-3 weeks after planting, while transplants are inoculated 1-3 days after planting. The test inoculum is produced from eggs from *H. glycines* cysts collected from the soil and roots of infested soybean plants. A 250 micron mesh sieve is used to collect the cysts, which are then crushed in a Tenbroeck glass tissue homogenizer to release the eggs. The eggs are further purified by sieving and centrifugation over 40 percent sucrose solution at 4000 RPM (revolutions per minute) for 5 minutes. Inoculum for an experiment consists of water containing approximately 500 vermiform eggs per mL. Five mL of the egg suspension is applied over the surface of the sand containing the test plants and the eggs are lightly watered into the sand. The test plants are then returned to the greenhouse or growth chamber and incubated for 3-4 weeks to allow for root infection and cyst formation. The roots are then harvested by gently removing the pot and sand and rinsing in water. The severity of nematode infection is measured by counting the number of nematode cysts adhering to the root system. Alternatively, the sand and roots could be diluted in water and passed over a 250 micron sieve to collect and concentrate the cysts for storage or counting.

The nematode modifies cells in the roots when establishing cellular feeding sites. Cells transformed with a viral enhancer segment linked 5' to a plant PRP promoter as described herein preferentially express high levels of the dsRNA targeting the suppression of the top-1 gene of the nematode. The exact cell type that SCN requires to create syncytium is not clearly elucidated, however, it is generally thought that vascular cells, stele and cortex cells are used by the nematode to create these feeding sites, therefore, expression of nematode control molecules in these cell types is especially important. The nematodes feeding on the soybean plant cells ingest the dsRNA molecule and are inhibited from further feeding resulting in the reduction of nematode induced plant disease symptoms. The resulting reduction in disease symptoms provides an increase in yield of soybean seed, soybean oil, and soybean protein, resulting in a decrease over time in the number of soy cyst nematodes present in the crop field.

Promoters of the present invention, in particular the PRP promoters as set forth at SEQ ID NOs:3-6 and SEQ ID NOs:44-47, and the chimeric promoters as set forth at SEQ ID NO:19-27, are operably linked to a polynucleotide molecule transcribing a mRNA that encodes an insecticidal protein, for example, a *Bacillus thuringiensis* (Bt) protein, or to a polynucleotide molecule that encodes the expression of one or more dsRNA molecules targeting the suppression of one or more corn rootworm (*Diabrotica* species) essential genes by RNAi. For example, a polynucleotide molecule that has a polynucleotide sequence that comprises a segment of a V-ATPase coding sequence specifically isolated from a corn rootworm DNA library (US Patent Publication No. 2007-0124836A1). The chimeric promoter is preferably selected to provide expression of a linked polynucleotide molecule in corn cells that are the preferred for corn rootworm feeding. For example, a viral enhancer linked to a monocot plant Prp promoter molecule that includes, but is not limited to SEQ ID NO:21, 22 or 27. The chimeric promoter/dsRNA V-ATPase molecule is inserted into a plant transformation vector, and transgenic corn cells are regenerated into plants that express the dsRNA molecules in the root tissues. The corn plants are provided in the diet of corn rootworms, which feed on the cells of the corn roots and ingest the dsRNA molecules. The transgenic corn plants are infested with corn rootworm larvae, root damage is rated 10-14 days after infestation with the larvae. The corn rootworms are inhibited from further feeding as a result of the effects of RNAi upon the expression of the targeted essential gene, V-ATPase, in the worm cells, resulting in the protection of the corn plant roots from corn rootworm feeding damage and an enhancement of yield and stress tolerance and crop plant standability.

DNA constructs comprising the PRP promoters of the present invention, in particular the chimeric promoters comprising PRP promoters as set forth at SEQ ID NO:19-20, and 23-26, operably linked to a fungal control molecule are transformed into soybean cells and the cells regenerated into transgenic soybean plants and individual soybean events selected. Of particular importance to soybean production is control of Asian soybean rust fungus (*Phakopsora pachyrhizi*). Asian soybean rust is a foliar pathogen that can cause defoliation of infected plants and severe yield losses. Transgenic soybean plants can be assayed for resistance to removing leaves from the transgenic soybean plants from the third or forth trifoliate which have been unfurled for about seven days. Three, 3 centimeter X 3.2 centimeter pieces of Whatman #1 filter paper are placed in each of 6 wells of a 6-well tissue culture plate (well volume is 15.5 milliliters). The leaves are cut into 3 centimeter by 3 centimeter pieces and placed on top of the Whatman filter papers with the bottom (stomatal side) of the leaf facing upwards. About 5 milliliters of sterile deionized water is put into each well of the 6-well tissue culture plate. Asian soybean rust urediniospores are suspended in sterile deionized water containing 0.01% TWEEN 20 at a concentration of 1×105 urediniospores per milliliter. Approximately 50 microliters of spore suspension is applied to each leaf piece using an airbrush (Model Badger 155 Anthem, Badger Air-Brush Co., Franklin Park, Ill.) with a compressor (Model TC-20, Airbrush Depot, San Diego, Calif.) setting of 1 kilogram per square centimeter to complete wetness. The 6-well plate is then sealed with PARAFILM and placed in a growth chamber set to 22 degrees Celsius, with a photoperiod of 12 hours day length and relative humidity at around 80%. The plates are checked every 2 or 3 days to monitor the progression of disease and to assure the wells have not dried out. Deionized water is added to make up the original volume in the well when needed. Early symptoms of developing lesions should be evident under a dissecting microscope about 3 to 5 days after inoculation. Sporulating lesions should be evident 9 to 14 days after inoculation. Average soybean rust disease severity scores are calculated from multiple trials. The rust severity score uses a rating scale from 1 to 5; 1—being immune, 2—demonstrating redibrown lesions over less than 50% of the leaf area, 3—demonstrating redibrown lesions over greater than 50% of the leaf area, 4—demonstrating tan lesions over less than 50% of the leaf area and 5—demonstrating tan lesions over greater than 50% of the leaf area. Control, uninfected leaf sections can remain viable in this assay for up to 2 months. Transgenic soybean events with low disease scores are grown to maturity and seeds collected, the seeds are planted in pots of soil and tested in a whole plant assay in a growth chamber for Asian Soybean Rust resistance. Events that show low disease scores in the growth chamber assay are grown to maturity and seeds collected and for use in a breeding program to introgress the disease resistance trait into elite soybean germplasm.

The present invention thus provides a DNA construct comprising a chimeric promoter molecule comprising a viral promoter enhancer segment linked preferentially 5' to a plant Prp promoter segment that can modulate expression of an operably linked transcribable polynucleotide molecule, and a transgenic plant and seed stably transformed with the DNA construct. The DNA construct can be used to express a transgene in plants that provides an agronomically important trait.

Alternatively, root enhanced expression from a plant PRP promoter segment, particularly a segment such as that set forth at SEQ ID NO:3, SEQ ID NO:4, SEQ ID NO:5, and SEQ ID NO:6, or SEQ ID NOs:44-47 is provided. Expression from such a promoter provides for accumulation of any agronomically important molecule preferentially in the root tissues of a plant.

Having illustrated and described the embodiments and principles of the present invention, it should be apparent to persons skilled in the art that the invention can be modified in arrangement and detail without departing from the spirit and scope of the invention. We claim all modifications that are within the spirit and scope of the appended claims. All publications and published patent documents cited in this specification are incorporated herein by reference to the same extent as if each individual publication or patent application is specifically and individually indicated to be incorporated by reference.

What is claimed is:

1. A method of reducing pest infestation or pathogen infection in a transgenic crop plant, the method comprising expressing in the plant an expression cassette comprising a (i) chimeric polynucleotide promoter molecule comprising in operable linkage 5' to 3' a plant viral promoter enhancer segment operably linked to a *Medicago* plant proline rich protein (Prp) promoter segment, which is (ii) operably linked to a nucleotide sequence that confers reduced pest infestation or reduced pathogen infection in the transgenic crop plant relative to a crop plant lacking the expression cassette,
    wherein the *Medicago* plant proline rich protein promoter comprises a polynucleotide sequence that exhibits at least 95 percent identity to SEQ ID NO:3, SEQ ID NO:4, SEQ ID NO:5, or SEQ ID NO:6; and
    wherein the pest or pathogen is selected from the group consisting of arthropods, nematodes, fungi, bacteria, oomycetes, and viruses.

2. The method of claim 1, wherein the arthropod is selected from the group consisting of Acarina, Coleoptera, Diptera, Hemiptera, Homoptera, Hymenoptera, Lepidoptera, Orthoptera, and Thysanoptera.

3. The method of claim 1, wherein the nematode is selected from the group consisting of Heteroderidae, Meloidogynidae, and Pratylenchidae.

4. The method of claim 1, wherein the fungus is selected from the group consisting of Uredinales, Ustilaginales, Erysiphales, Basidiomycetes, Ascomycetes, and Fungi Imperfecti.

5. The method of claim 1, wherein the bacterium is selected from the group consisting of *Pseudomonas, Xanthomonas, Erwinia*, and *Corynebacterium*.

6. The method of claim 1, wherein the virus is selected from the group consisting of Potyviruses, Luteoviruses, Geminiviruses, Ilarviruses, Comoviruses, Caulimoviruses, Cucumoviruses, Fijiviruses, Alfamoviruses, Badnaviruses, Bromoviruses, Furoviruses, Tospoviruses, and To bamoviruses.

7. The method of claim 1, wherein the viral promoter enhancer molecule is selected from the group consisting of SEQ ID NO: 1, SEQ ID NO: 2, a fragment of SEQ ID NO:1 comprising an enhancer domain, and a fragment of SEQ ID NO:2 comprising an enhancer domain.

8. The method of claim 1, wherein the chimeric polynucleotide promoter molecule comprises a sequence that exhibits at least 90 percent identity to SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO:27.

\* \* \* \* \*